US009267156B2

(12) United States Patent
Amano et al.

(10) Patent No.: US 9,267,156 B2
(45) Date of Patent: Feb. 23, 2016

(54) ISOPROPYL ALCOHOL-PRODUCING BACTERIUM HAVING IMPROVED PRODUCTIVITY BY GNTR DESTRUCTION

(75) Inventors: Koh Amano, Mobara (JP); Tomokazu Shirai, Yokohama (JP); Hitoshi Takahashi, Chiba (JP); Junichiro Hirano, Tokyo (JP); Yoshiko Matsumoto, Mobara (JP); Nozomi Takebayashi, Mobara (JP); Mitsufumi Wada, Chiba (JP); Hiroshi Shimizu, Ibaraki (JP); Chikara Furusawa, Ibaraki (JP); Takashi Hirasawa, Minoh (JP)

(73) Assignee: MITSUI CHEMICALS, INC., Tokyo (JP)

( * ) Notice: Subject to any disclaimer, the term of this patent is extended or adjusted under 35 U.S.C. 154(b) by 486 days.

(21) Appl. No.: 13/816,077

(22) PCT Filed: Aug. 11, 2011

(86) PCT No.: PCT/JP2011/068402
§ 371 (c)(1),
(2), (4) Date: Feb. 8, 2013

(87) PCT Pub. No.: WO2012/020833
PCT Pub. Date: Feb. 16, 2012

(65) Prior Publication Data
US 2013/0211170 A1    Aug. 15, 2013

(30) Foreign Application Priority Data

Aug. 12, 2010  (JP) ................................. 2010-181150
Mar. 7, 2011    (JP) ................................. 2011-049531

(51) Int. Cl.
C12P 7/04        (2006.01)
C07C 1/24        (2006.01)
C07K 14/245      (2006.01)
C12N 15/70       (2006.01)
C12P 7/28        (2006.01)
C07C 45/00       (2006.01)
C12N 9/04        (2006.01)
C12N 9/88        (2006.01)

(52) U.S. Cl.
CPC ... *C12P 7/04* (2013.01); *C07C 1/24* (2013.01); *C07C 45/002* (2013.01); *C07K 14/245* (2013.01); *C12N 9/0006* (2013.01); *C12N 9/88* (2013.01); *C12N 15/70* (2013.01); *C12P 7/28* (2013.01); *C07C 2529/70* (2013.01); *Y02P 20/52* (2015.11)

(58) Field of Classification Search
None
See application file for complete search history.

(56) References Cited

U.S. PATENT DOCUMENTS

| 5,281,531 A | 1/1994 | Miyagawa et al. |
| 2009/0246842 A1 | 10/2009 | Hawkins et al. |
| 2010/0203604 A1 | 8/2010 | Yukawa et al. |
| 2010/0221800 A1 | 9/2010 | Liao et al. |
| 2010/0311135 A1* | 12/2010 | Takebayashi et al. ........ 435/157 |

FOREIGN PATENT DOCUMENTS

| DE | 84 378 | 12/1971 |
| GB | 665376 A | 1/1952 |
| JP | 02-174737 | 7/1990 |
| JP | 05-260979 | 10/1993 |
| JP | 07-053433 | 2/1995 |
| JP | 11-335315 | 12/1999 |
| JP | 2009-247217 | 10/2009 |
| WO | WO 2009/008377 A1 | 1/2009 |
| WO | WO 2009/028582 A1 | 3/2009 |
| WO | WO 2009/049274 A2 | 4/2009 |
| WO | WO 2009/103026 A1 | 8/2009 |
| WO | WO-2010/064500 A1 | 6/2010 |

OTHER PUBLICATIONS

Extended European Search Report issued in European Application No. 11816495.3 dated Oct. 7, 2014.
Peekhaus et al. "Positive and negative transcriptional regulation of the *Escherichia coli* gluconate regulon gene gntT by GntR and the cyclic AMP (cAMP) cAMP receptor protein complex." Journal of Bacteriology, vol. 180, No. 7, Apr. 1998, pp. 1777-1785, XP055140873.
Yoshida K-I et al. "Missense Mutations in the Bacillus subtilis gnt Repressor that Diminish Operator Binding Ability", Journal of Molecular Biology, Academic Press, United Kingdom, vol. 231, No. 2, May 20, 1993, pp. 167-174, XP024008960.
Chinese First Office Action for application No. 201180038987.0 dated Oct. 12, 2013 (with partial English translation).
International Search Report PCT/JP2011/068402 dated Oct. 11, 2011.
T. Hanai et al., "Engineered Synthetic Pathway for Isopropanol Production in *Escherichia coli*", Applied Environmental Microbiology, vol. 73, No. 24, Dec. 2007, pp. 7814-7818.
Toru Jojima et al., "Production of isopropanol by metabolically engineered *Escherichia coli*", Appl. Microbiol. Biotechnol. (2008) 77:1219-1224.

* cited by examiner

*Primary Examiner* — Alexander Kim
(74) *Attorney, Agent, or Firm* — Foley & Lardner LLP

(57) ABSTRACT

An isopropyl alcohol-producing *Escherichia coli* includes an isopropyl alcohol production system, wherein an activity of transcriptional repressor GntR is inactivated, and the isopropyl alcohol-producing *Escherichia coli* preferably further includes a group of auxiliary enzymes having an enzyme activity expression pattern with which isopropyl alcohol production capacity achieved by the inactivation of the GntR activity is maintained or enhanced. A method of producing isopropyl alcohol includes producing isopropyl alcohol from a plant-derived raw material using the isopropyl alcohol-producing *Escherichia coli*. A method of producing acetone includes contacting the isopropyl alcohol obtained by the isopropyl alcohol production method with a complex oxide that includes zinc oxide and at least one oxide containing a Group 4 element, and that is prepared by coprecipitation. A method of producing propylene includes contacting isopropyl alcohol and acetone obtained by the production method with a solid acidic substance and a Cu-containing hydrogenation catalyst as catalysts.

14 Claims, No Drawings

SEQUENCE LISTING

<160> NUMBER OF SEQ ID NOS: 49

<210> SEQ ID NO 1
<211> LENGTH: 30
<212> TYPE: DNA
<213> ORGANISM: Artificial
<220> FEATURE:
<223> OTHER INFORMATION: primer

<400> SEQUENCE: 1
cgctcaattg caatgattga cacgattccg               30

<210> SEQ ID NO 2
<211> LENGTH: 32
<212> TYPE: DNA
<213> ORGANISM: Artificial
<220> FEATURE:
<223> OTHER INFORMATION: primer

<400> SEQUENCE: 2
acagaattcg ctatttgtta gtgaataaaa gg             32

```
<210> SEQ ID NO 3
<211> LENGTH: 50
<212> TYPE: DNA
<213> ORGANISM: Artificial
<220> FEATURE:
<223> OTHER INFORMATION: primer

<400> SEQUENCE: 3
cgaattcgct ggtggaacat atgaaaacaa aattgatgac attacaagac          50

<210> SEQ ID NO 4
<211> LENGTH: 30
<212> TYPE: DNA
<213> ORGANISM: Artificial
<220> FEATURE:
<223> OTHER INFORMATION: primer

<400> SEQUENCE: 4
gcggtacctt atttgctctc ctgtgaaacg                                30

<210> SEQ ID NO 5
<211> LENGTH: 31
<212> TYPE: DNA
<213> ORGANISM: Artificial
<220> FEATURE:
<223> OTHER INFORMATION: primer

<400> SEQUENCE: 5
gctctagatg ctgaaatcca ctagtcttgt c                              31

<210> SEQ ID NO 6
<211> LENGTH: 29
<212> TYPE: DNA
<213> ORGANISM: Artificial
<220> FEATURE:
<223> OTHER INFORMATION: primer

<400> SEQUENCE: 6
tactgcagcg ttccagcacc ttatcaacc                                 29

<210> SEQ ID NO 7
<211> LENGTH: 29
<212> TYPE: DNA
<213> ORGANISM: Artificial
<220> FEATURE:
<223> OTHER INFORMATION: primer

<400> SEQUENCE: 7
ggtctagagc aatgattgac acgattccg                                 29

<210> SEQ ID NO 8
<211> LENGTH: 45
<212> TYPE: DNA
<213> ORGANISM: Artificial
<220> FEATURE:
<223> OTHER INFORMATION: primer

<400> SEQUENCE: 8
aatatgcatg ctggtggaac atatgaaagg ttttgcaatg ctagg               45

<210> SEQ ID NO 9
<211> LENGTH: 38
<212> TYPE: DNA
<213> ORGANISM: Artificial
<220> FEATURE:
<223> OTHER INFORMATION: primer
```

<400> SEQUENCE: 9
gcggatcctt ataataac tactgcttta attaagtc                              38

<210> SEQ ID NO 10
<211> LENGTH: 54
<212> TYPE: DNA
<213> ORGANISM: Artificial
<220> FEATURE:
<223> OTHER INFORMATION: primer

<400> SEQUENCE: 10
caggatccgc tggtggaaca tatgttaaag gatgaagtaa ttaaacaaat tagc           54

<210> SEQ ID NO 11
<211> LENGTH: 43
<212> TYPE: DNA
<213> ORGANISM: Artificial
<220> FEATURE:
<223> OTHER INFORMATION: primer

<400> SEQUENCE: 11
ggaattcggt accttactta agataatcat ataaacttc agc                       43

<210> SEQ ID NO 12
<211> LENGTH: 46
<212> TYPE: DNA
<213> ORGANISM: Artificial
<220> FEATURE:
<223> OTHER INFORMATION: primer

<400> SEQUENCE: 12
caggatcccg gagaaagtct tatggcggta acgcaaacag cccagg                   46

<210> SEQ ID NO 13
<211> LENGTH: 34
<212> TYPE: DNA
<213> ORGANISM: Artificial
<220> FEATURE:
<223> OTHER INFORMATION: primer

<400> SEQUENCE: 13
cgtctagatt actcaaactc attccaggaa cgac                                34

<210> SEQ ID NO 14
<211> LENGTH: 29
<212> TYPE: DNA
<213> ORGANISM: Artificial
<220> FEATURE:
<223> OTHER INFORMATION: primer

<400> SEQUENCE: 14
caggaattcg ctatatctgg ctctgcacg                                      29

<210> SEQ ID NO 15
<211> LENGTH: 31
<212> TYPE: DNA
<213> ORGANISM: Artificial
<220> FEATURE:
<223> OTHER INFORMATION: primer

<400> SEQUENCE: 15
cagtctagag caatactctt ctgattttga g                                   31

<210> SEQ ID NO 16

```
<211> LENGTH: 29
<212> TYPE: DNA
<213> ORGANISM: Artificial
<220> FEATURE:
<223> OTHER INFORMATION: primer

<400> SEQUENCE: 16
cagtctagat catcgtcgat atgtaggcc                                              29

<210> SEQ ID NO 17
<211> LENGTH: 29
<212> TYPE: DNA
<213> ORGANISM: Artificial
<220> FEATURE:
<223> OTHER INFORMATION: primer

<400> SEQUENCE: 17
gacctgcaga tcatccgtca gctgtacgc                                              29

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
cgagctacat atgcaatgat tgacacgatt ccg                                         33

<210> SEQ ID NO 19
<211> LENGTH: 32
<212> TYPE: DNA
<213> ORGANISM: Artificial
<220> FEATURE:
<223> OTHER INFORMATION: primer

<400> SEQUENCE: 19
cgcgcgcatg ctatttgtta gtgaataaaa gg                                          32

<210> SEQ ID NO 20
<211> LENGTH: 45
<212> TYPE: DNA
<213> ORGANISM: Artificial
<220> FEATURE:
<223> OTHER INFORMATION: primer

<400> SEQUENCE: 20
aatatgcatg ctggtggaac atatgaaagg ttttgcaatg ctagg                            45

<210> SEQ ID NO 21
<211> LENGTH: 44
<212> TYPE: DNA
<213> ORGANISM: Artificial
<220> FEATURE:
<223> OTHER INFORMATION: primer

<400> SEQUENCE: 21
gcggatccgg taccttataa tataactact gctttaatta agtc                             44

<210> SEQ ID NO 22
<211> LENGTH: 44
<212> TYPE: DNA
<213> ORGANISM: Artificial
<220> FEATURE:
<223> OTHER INFORMATION: primer

<400> SEQUENCE: 22
```

```
atggatccgc tggtggaaca tatgaaaaat tgtgtcatcg tcag        44
```

<210> SEQ ID NO 23
<211> LENGTH: 42
<212> TYPE: DNA
<213> ORGANISM: Artificial
<220> FEATURE:
<223> OTHER INFORMATION: primer

<400> SEQUENCE: 23

```
gcagaagctt gtctagatta attcaaccgt tcaatcacca tc          42
```

<210> SEQ ID NO 24
<211> LENGTH: 51
<212> TYPE: DNA
<213> ORGANISM: Artificial
<220> FEATURE:
<223> OTHER INFORMATION: primer

<400> SEQUENCE: 24

```
gctctagagc tggtggaaca tatgaaaaca aaattgatga cattacaaga c    51
```

<210> SEQ ID NO 25
<211> LENGTH: 41
<212> TYPE: DNA
<213> ORGANISM: Artificial
<220> FEATURE:
<223> OTHER INFORMATION: primer

<400> SEQUENCE: 25

```
tagcaagctt ctactcgagt tatttgctct cctgtgaaac g           41
```

<210> SEQ ID NO 26
<211> LENGTH: 44
<212> TYPE: DNA
<213> ORGANISM: Artificial
<220> FEATURE:
<223> OTHER INFORMATION: primer

<400> SEQUENCE: 26

```
aagtctcgag ctggtggaac atatggatgc gaaacaacgt attg        44
```

<210> SEQ ID NO 27
<211> LENGTH: 28
<212> TYPE: DNA
<213> ORGANISM: Artificial
<220> FEATURE:
<223> OTHER INFORMATION: primer

<400> SEQUENCE: 27

```
ggccaagctt cataaatcac cccgttgc                          28
```

<210> SEQ ID NO 28
<211> LENGTH: 54
<212> TYPE: DNA
<213> ORGANISM: Artificial
<220> FEATURE:
<223> OTHER INFORMATION: primer

<400> SEQUENCE: 28

```
caggtaccgc tggtggaaca tatgttaaag gatgaagtaa ttaaacaaat tagc    54
```

<210> SEQ ID NO 29
<211> LENGTH: 38
<212> TYPE: DNA

```
<213> ORGANISM: Artificial
<220> FEATURE:
<223> OTHER INFORMATION: primer

<400> SEQUENCE: 29
gcggatcctt acttaagata atcatatata acttcagc                               38

<210> SEQ ID NO 30
<211> LENGTH: 29
<212> TYPE: DNA
<213> ORGANISM: Artificial
<220> FEATURE:
<223> OTHER INFORMATION: primer

<400> SEQUENCE: 30
ggaattcggg tcaattttca ccctctatc                                         29

<210> SEQ ID NO 31
<211> LENGTH: 37
<212> TYPE: DNA
<213> ORGANISM: Artificial
<220> FEATURE:
<223> OTHER INFORMATION: primer

<400> SEQUENCE: 31
gtgggccgtc ctgaaggtac aaaagagata gattctc                                37

<210> SEQ ID NO 32
<211> LENGTH: 37
<212> TYPE: DNA
<213> ORGANISM: Artificial
<220> FEATURE:
<223> OTHER INFORMATION: primer

<400> SEQUENCE: 32
ctcttttgta ccttcaggac ggcccacaaa tttgaag                                37

<210> SEQ ID NO 33
<211> LENGTH: 29
<212> TYPE: DNA
<213> ORGANISM: Artificial
<220> FEATURE:
<223> OTHER INFORMATION: primer

<400> SEQUENCE: 33
ggaattccca gccccgcaag gccgatggc                                         29

<210> SEQ ID NO 34
<211> LENGTH: 31
<212> TYPE: DNA
<213> ORGANISM: Artificial
<220> FEATURE:
<223> OTHER INFORMATION: primer

<400> SEQUENCE: 34
cgccatatga atggcgcggc ggggccggtg g                                      31

<210> SEQ ID NO 35
<211> LENGTH: 28
<212> TYPE: DNA
<213> ORGANISM: Artificial
<220> FEATURE:
<223> OTHER INFORMATION: primer

<400> SEQUENCE: 35
tggagctctg tttactcctg tcaggggg                                          28
```

<210> SEQ ID NO 36
<211> LENGTH: 33
<212> TYPE: DNA
<213> ORGANISM: Artificial
<220> FEATURE:
<223> OTHER INFORMATION: primer

<400> SEQUENCE: 36
tggagctctc tgatttaatc aacaataaaa ttg                              33

<210> SEQ ID NO 37
<211> LENGTH: 29
<212> TYPE: DNA
<213> ORGANISM: Artificial
<220> FEATURE:
<223> OTHER INFORMATION: primer

<400> SEQUENCE: 37
cgggatccac caccataacc aaacgacgg                                   29

<210> SEQ ID NO 38
<211> LENGTH: 33
<212> TYPE: DNA
<213> ORGANISM: Artificial
<220> FEATURE:
<223> OTHER INFORMATION: primer38

<400> SEQUENCE: 38
cgagctacat atgcaatgat tgacacgatt ccg                              33

<210> SEQ ID NO 39
<211> LENGTH: 32
<212> TYPE: DNA
<213> ORGANISM: Artificial
<220> FEATURE:
<223> OTHER INFORMATION: primer39

<400> SEQUENCE: 39
cgcgcgcatg ctatttgtta gtgaataaaa gg                               32

<210> SEQ ID NO 40
<211> LENGTH: 1056
<212> TYPE: DNA
<213> ORGANISM: Clostridium beijerinckii

<400> SEQUENCE: 40
atgaaaggtt ttgcaatgct gggtattaat aagctgggct ggatcgaaaa agagcgcccg    60
gttgcgggtt cgtatgatgc gattgtgcgc ccactggccg tatctccgtg tacctcagat   120
atccataccg tttttgaggg agctcttggc gaccgcaaga atatgatttt agggcatgaa   180
gcggtgggtg aagttgtgga ggtaggcagt gaagtgaagg atttcaaacc tggtgaccgt 240
gttatcgtcc cttgcacaac cccggattgg cggtctttgg aagttcaggc tggttttcaa 300
cagcactcaa acggtatgct cgcaggatgg aaattttcca acttcaagga tggcgtcttt 360
ggtgagtatt ttcatgtgaa tgatgcggat atgaatcttg cgattctgcc taaagacatg 420
cccctggaaa acgctgttat gatcacagat atgatgacta cgggcttcca cggagccgaa 480
cttgcagata ttcagatggg ttcaagtgta gtggtcattg gcattggcgc ggttggcctg 540
atggggatag ccggtgctaa attacgtgga gcaggtcgga tcattggcgt ggggagccgc 600
ccgatttgtg tcgaggctgc caaattttac ggggccaccg acattttgaa ttataaaaat 660

```
ggtcatatcg ttgatcaagt catgaaactg acgaacggaa aaggcgttga ccgcgtgatt    720
atggcaggcg gtggtagcga aacactgtcc caggccgtat ctatggtcaa accaggcggg    780
atcatttcga atataaatta tcatggaagt ggcgatgcgt tattgatccc gcgtgtggaa    840
tgggggtgcg gaatggctca caagactatc aaaggcggtc tttgtcccgg gggacgtttg    900
agagcagaga tgctgcgaga tatggtagtg tacaaccgtg ttgatctcag caaactggtc    960
acgcatgtat atcatgggtt cgatcacatc gaagaagccc tgttactgat gaaagacaag   1020
ccaaaagacc tgattaaagc agtagttata ttataa                             1056
```

<210> SEQ ID NO 41
<211> LENGTH: 31
<212> TYPE: DNA
<213> ORGANISM: Artificial
<220> FEATURE:
<223> OTHER INFORMATION: primer41

<400> SEQUENCE: 41

```
acatgcatgc atgaaaggtt ttgcaatgct g                                    31
```

<210> SEQ ID NO 42
<211> LENGTH: 33
<212> TYPE: DNA
<213> ORGANISM: Artificial
<220> FEATURE:
<223> OTHER INFORMATION: primer42

<400> SEQUENCE: 42

```
acgcgtcgac ttataatata actactgctt taa                                  33
```

<210> SEQ ID NO 43
<211> LENGTH: 735
<212> TYPE: DNA
<213> ORGANISM: Clostridium acetobutylicum

<400> SEQUENCE: 43

```
atgctgaaag atgaagtgat taaacagatt agcacgccat taacttcgcc tgcatttccg     60
cgcggtccgt ataaatttca taatcgtgaa tattttaaca ttgtataccg taccgatatg    120
gacgccctgc gtaaagttgt gccagagcct ctggaaattg atgagccctt agtccggttc    180
gaaatcatgg caatgcatga tacgagtggc ctgggttgct atacagaatc aggtcaggct    240
attcccgtga gctttaatgg tgttaagggc gactaccttc acatgatgta tctggataac    300
gagccggcaa ttgccgtagg tcgggaatta agtgcatacc ctaaaaagct cgggtatcca    360
aagctgtttg tggattcaga cactctggtg ggcacgttag actatggaaa actgcgtgtt    420
gcgaccgcga caatgggta caaacataaa gccctggatg ctaatgaagc aaaggatcaa    480
atttgtcgcc cgaactatat gttgaaaatc atccccaatt atgacggctc ccctcgcata    540
tgcgagctta tcaacgcgaa aatcaccgat gttaccgtac atgaagcttg gacaggaccg    600
actcgactgc agttattcga tcacgctatg gcgccactga tgacttgcc ggtcaaagag    660 attgtttcta gctctcacat tcttgccgat ataatcttgc cgcgcgcgga agtcatatac    720
gattatctca agtaa                                                     735
```

<210> SEQ ID NO 44
<211> LENGTH: 49
<212> TYPE: DNA
<213> ORGANISM: Artificial
<220> FEATURE:
<223> OTHER INFORMATION: primer44

```
<400> SEQUENCE: 44
acgcgtcgac gctggttggt ggaacatatg ctgaaagatg aagtgatta         49

<210> SEQ ID NO 45
<211> LENGTH: 31
<212> TYPE: DNA
<213> ORGANISM: Artificial
<220> FEATURE:
<223> OTHER INFORMATION: primer45

<400> SEQUENCE: 45
gctctagatt acttgagata atcgtatatg a                           31

<210> SEQ ID NO 46
<211> LENGTH: 46
<212> TYPE: DNA
<213> ORGANISM: Artificial
<220> FEATURE:
<223> OTHER INFORMATION: primer46

<400> SEQUENCE: 46
gctctagacg gagaaagtct tatggcggta acgcaaacag cccagg           46

<210> SEQ ID NO 47
<211> LENGTH: 34
<212> TYPE: DNA
<213> ORGANISM: Artificial
<220> FEATURE:
<223> OTHER INFORMATION: primer47

<400> SEQUENCE: 47
cgggatcctt actcaaactc attccaggaa cgac                        34

<210> SEQ ID NO 48
<211> LENGTH: 35
<212> TYPE: DNA
<213> ORGANISM: Artificial
<220> FEATURE:
<223> OTHER INFORMATION: primer48

<400> SEQUENCE: 48
gctggtggaa catatgacgc aatctcgatt gcatg                       35

<210> SEQ ID NO 49
<211> LENGTH: 21
<212> TYPE: DNA
<213> ORGANISM: Artificial
<220> FEATURE:
<223> OTHER INFORMATION: primer49

<400> SEQUENCE: 49
ttaacccagt tgccagagtg c                                      21
```

ISOPROPYL ALCOHOL-PRODUCING BACTERIUM HAVING IMPROVED PRODUCTIVITY BY GNTR DESTRUCTION

TECHNICAL FIELD

The present invention relates to an isopropyl alcohol-producing bacterium and a method of producing isopropyl alcohol using the bacterium.

BACKGROUND ART

Propylene is an important basic raw material for synthetic resins such as polypropylene and for petrochemical products, and is used widely such as for automobile bumpers, food containers, films, and medical instruments.

Isopropyl alcohol produced from plant-derived raw materials can be converted to propylene through a dehydration process. Therefore, isopropyl alcohol is a promising carbon-neutral raw material for propylene. Acetone is also widely used as solvents and raw materials for plastics. Kyoto Protocol called for industrialized nations to reduce their total carbon dioxide emissions from 1990 levels by 5 percent by 2008-2012. Therefore, carbon-neutral propylene is currently extremely important due to its versatility, in view of the global environment.

Bacteria that assimilate plant-derived raw materials and produce isopropyl alcohol are already known. For example, WO 2009/008377 discloses a bacterium that is modified to produce isopropyl alcohol using glucose as a raw material, and describes that the bacterium has excellent properties as a biocatalyst for industrial production due to its high selectivity for isopropyl alcohol.

In isopropyl alcohol-producing *Escherichia coli*, because the raw material for isopropyl alcohol is glucose, a great number of compounds formed by glycolysis and catabolism can all be by-products. However, these compounds are essential substances for the growth of *Escherichia coli* in some cases, and, therefore, the amount of glucose consumed by these side reactions cannot be completely eliminated. Accordingly, various studies have been carried out with a view to minimizing the by-products and increasing the amount of isopropyl alcohol produced.

For example, WO 2009/008377 pamphlet discloses an isopropyl alcohol-producing bacterium to which acetoacetate decarboxylase, isopropyl alcohol dehydrogenase, CoA transferase and thiolase genes have been introduced, and which is capable of producing isopropyl alcohol form a plant-derived raw material. It is described that the capacity of the isopropyl alcohol-producing bacterium provides a production rate of 0.6 g/L/hr and an accumulation amount of 28.4 g/L.

WO 2009/049274 and *Appl. Environ. Biotechnol.*, 73(24), pp. 7814-7818, (2007) disclose an *Escherichia coli* variant to which acetyl-CoA acetyltransferase, acetoacetyl-CoA transferase, acetoacetate decarboxylase and secondary alcohol dehydrogenase genes have been introduced, and which produces isopropyl alcohol. It is described that the capacity of the bacteria provides a production rate of 0.4 g/L/hr, a yield of 43.5%, and an accumulation amount of 4.9 g/L.

WO 2009/028582 discloses an *Escherichia coli* variant to which acetoacetate decarboxylase, isopropyl alcohol dehydrogenase, acetyl CoA:acetate CoA-transferase and acetyl-CoA acetyltransferase genes have been introduced, and which produces isopropyl alcohol. It is described that the capacity of the bacterium provides an accumulation amount of 9.7 g/L.

*Appl. Microbiol. Biotechnol.*, 77(6), pp. 1219-1224, (2008) discloses an *Escherichia coli* variant to which thiolase, CoA-transferase, acetoacetate decarboxylase and primary-secondary alcohol dehydrogenase genes have been introduced, and which produces isopropyl alcohol. It is described that the capacity of the bacterium provides a production rate of 0.6 g/L/hr, a yield of 51% and an accumulation amount of 13.6 g/L.

WO 2009/103026 discloses an *Escherichia coli* variant to which acetoacetate decarboxylase, acetyl CoA:acetate CoA-transferase, acetyl-CoA acetyltransferase and isopropyl alcohol dehydrogenase genes have been introduced, and which is capable of producing isopropyl alcohol. It is described that the bacterium is expected to have a capacity that provides a yield of 50%, a production rate of 0.4 g/L/hr and a final production amount of 14 g/L.

WO 2009/247217 discloses an *Escherichia coli* variant to which acetoacetate decarboxylase, CoA transferase, thiolase and 2-propyl alcohol dehydrogenase genes have been introduced, and which is capable of producing isopropyl alcohol. It is described that the capacity of the bacterium provides a final production amount of 2 g/L.

Here, isopropyl alcohol dehydrogenase, secondary alcohol dehydrogenase, primary-secondary alcohol dehydrogenase and 2-propyl alcohol dehydrogenase are enzymes that have different names but catalyze the same reaction. CoA transferase, acetoacetyl-CoA transferase, acetyl CoA:acetate CoA-transferase and CoA transferase are enzymes that have different names but catalyze the same reaction. Acetoacetic acid decarboxylase and acetoacetate decarboxylase are enzymes that have different names but catalyze the same reaction. Thiolase and acetyl-CoA acetyltransferase are enzymes that have different names but catalyze the same reaction. Accordingly, although the productivity of the isopropyl alcohol-producing *Escherichia coli* variants disclosed in these documents varies, the enzymes utilized for producing isopropyl alcohol are equivalent to the four types of enzymes of acetoacetate decarboxylase, isopropyl alcohol dehydrogenase, CoA transferase and thiolase, which are described in WO 2009/008377. In a case in which it is desired to improve the productivity or yield, these four types of enzymes have been examined thus far.

Japanese Patent Application Laid-Open (JP-A) No. 5-260979 describes that, in *Bacillus subtillis*, disruption of GntR gene possessed by the *Escherichia coli* improves production of D-ribose.

Further, with regard to a method for converting isopropyl alcohol into acetone, a copper-based catalyst is used as a solid catalyst for production of acetone through dehydrogenation of isopropyl alcohol in JP-A No. 7-53433 and JP-A No. 11-335315. Moreover, a catalyst obtained by physical mixing of zinc oxide fine particles and zirconium oxide fine particles is used in UK Patent No. GB665376. It is known that impurities are generally contained when a substance is produced using a microorganism. In this regard, none of these techniques is a production method using microorganisms, and, therefore, does not describe that impurity-containing isopropanol is used as a raw material Acetone can easily be converted into isopropanol by hydrogenation. A process has been proposed (see, for example, JP-A No. 2-174737) which includes obtaining propylene from the isopropanol via a dehydration reaction, and thereafter obtaining cumene by allowing the propylene to react with benzene, that is, a process in which acetone is reused as a raw material for the Cumene method by being converted into propylene via two-step reactions.

In the re-usage as described above, there is a need for establishment of an industrial and practical method for producing propylene from acetone with high selectivity. A method is also known (see, for example, East Germany Patent No. DD84378) which includes carrying out a hydrogenation reaction of acetone at 400° C. in the presence of a Cu (25%)-zinc oxide (35%)-aluminum oxide (40%) catalyst to obtain propylene. However, although the reaction temperature in this method is high (400° C.), the conversion rate of acetone is low (89%). In addition, since a side reaction that generates propane via hydrogenation of propylene occurs in the method, the propylene selectivity is also insufficient (89%).

SUMMARY OF INVENTION

Technical Problem

However, none of the above-described *Escherichia coli* variants capable of producing isopropyl alcohol has a fully satisfactory production capacity. Improvement of efficiency in production of isopropyl alcohol in isopropyl alcohol-producing *Escherichia coli* has been a major target to be achieved. In addition, provision of a method for effective utilization of isopropyl alcohol obtained has also been desired.

An object of the present invention is to provide *Escherichia coli* having significantly efficiency of production of isopropyl alcohol, an isopropyl alcohol production method and an acetone production method which use the *Escherichia coli*, as well as a method of producing propylene from isopropyl alcohol which contains acetone and which is obtained using the *Escherichia coli*.

Solution to Problem

The present invention was made in view of the above-described circumstances. An isopropyl alcohol-producing *Escherichia coli* according to the invention, an isopropyl alcohol production method according to the invention, and an acetone production method according to the present invention are as described below.

[1] An isopropyl alcohol-producing *Escherichia coli* including an isopropyl alcohol production system, wherein the activity of transcriptional repressor GntR is inactivated, and the isopropyl alcohol-producing *Escherichia coli* includes a group of auxiliary enzymes having an enzyme activity pattern with which isopropyl alcohol production capacity achieved by the inactivation of the GntR activity is maintained or enhanced.

[2] The isopropyl alcohol-producing *Escherichia coli* according to [1], wherein the enzyme activity pattern of the group of auxiliary enzymes is selected from the group consisting of:

(1) maintenance of wild-type activities of glucose-6-phosphate isomerase (Pgi) activity, glucose-6-phosphate 1-dehydrogenase (Zwf) activity and phosphogluconate dehydrogenase (Gnd) activity;

(2) inactivation of glucose-6-phosphate isomerase (Pgi) activity and enhancement of glucose-6-phosphate 1-dehydrogenase (Zwf) activity; and (3) inactivation of glucose-6-phosphate isomerase (Pgi) activity, enhancement of glucose-6-phosphate 1-dehydrogenase (Zwf) activity and inactivation of phosphogluconate dehydrogenase (Gnd) activity.

[3] The isopropyl alcohol-producing *Escherichia coli* according to [2], wherein the glucose-6-phosphate 1-dehydrogenase (Zwf) activity is derived from a gene encoding glucose-6-phosphate 1-dehydrogenase (Zwf) derived from a bacterium of the genus *Escherichia*.

[4] The isopropyl alcohol-producing *Escherichia coli* according to any one of [1] to [3], wherein the isopropyl alcohol production system is constituted by enzyme genes of acetoacetate decarboxylase, isopropyl alcohol dehydrogenase, CoA transferase and thiolase.

[5] The isopropyl alcohol-producing *Escherichia coli* according to any one of [1] to [4], wherein the isopropyl alcohol production system is constituted by enzyme genes of acetoacetate decarboxylase, isopropyl alcohol dehydrogenase, CoA transferase and thiolase, and each of the enzyme genes is independently derived from at least one prokaryote selected from the group consisting of a bacterium of the genus *Clostridium*, a bacterium of the genus *Bacillus* and a bacterium of the genus *Escherichia*.

[6] The isopropyl alcohol-producing *Escherichia coli* according to [4] or [5], wherein the acetoacetate decarboxylase activity is derived from an enzyme-encoding gene derived from *Clostridium acetobutylicum*, the isopropyl alcohol dehydrogenase activity is derived from an enzyme-encoding gene derived from *Clostridium beijerinckii*, and the CoA transferase activity and the thiolase activity are derived from enzyme-encoding genes derived from *Escherichia coli*.

[7] The isopropyl alcohol-producing *Escherichia coli* according to [4], wherein at least one selected from the group consisting of the isopropyl alcohol dehydrogenase activity and the acetoacetate decarboxylase activity is derived from a gene or genes introduced as a modified gene or modified genes.

[8] The isopropyl alcohol-producing *Escherichia coli* according to [7], wherein the modified gene of the isopropyl alcohol dehydrogenase has a base sequence represented by SEQ ID NO: 40, and the modified gene of the acetoacetate decarboxylase has a base sequence represented by SEQ ID NO: 43.

[9] The isopropyl alcohol-producing *Escherichia coli* according to any one of [4] to [8], further including at least a sucrose hydrolase gene from among sucrose non-PTS genes.

[10] A method of producing isopropyl alcohol, including producing isopropyl alcohol from a plant-derived raw material using the isopropyl alcohol-producing *Escherichia coli* of any one of [1] to [9].

[11] A method of producing acetone, including:
obtaining isopropyl alcohol from a plant-derived raw material using the isopropyl alcohol-producing *Escherichia coli* of any one of [1] to [9]; and
contacting the obtained isopropyl alcohol with a complex oxide as a catalyst that includes zinc oxide and at least one oxide containing a Group 4 element, and that is prepared by coprecipitation.

[12] A method of producing propylene, including:
contacting isopropyl alcohol that is obtained from a plant-derived raw material using the isopropyl alcohol-producing *Escherichia coli* of any one of [1] to [9] and that contains acetone, with a solid acidic substance and a Cu-containing hydrogenation catalyst as catalysts, at a reaction temperature within a range of from 50 to 300° C.

[13] The method of producing propylene according to [12], wherein the Cu-containing hydrogenation catalyst is a catalyst that further includes at least one element selected from the group consisting of Group 6, Group 12 and Group 13 elements.

[14] The method of producing propylene according to [12] or [13], wherein the solid acidic substance is zeolite.

Advantageous Effect of Invention

According to the present invention, an *Escherichia coli* having significantly efficiency of production of isopropyl alcohol, an isopropyl alcohol production method and an acetone production method which use the *Escherichia coli*, as well as a method of producing propylene from isopropyl alcohol which contains acetone and which is obtained using the *Escherichia coli* can be provided.

DESCRIPTION OF EMBODIMENTS

An isopropyl alcohol-producing *Escherichia coli* of the present invention is an isopropyl alcohol-producing *Escherichia coli* including an isopropyl alcohol production system, wherein the activity of transcriptional repressor GntR is inactivated, and the isopropyl alcohol-producing *Escherichia coli* includes a group of auxiliary enzymes having an enzyme activity pattern with which isopropyl alcohol production capacity achieved by the inactivation of the GntR activity is maintained or enhanced.

In the isopropyl alcohol-producing *Escherichia coli* according to the invention, the inactivation of the GntR activity in combination with the possession of a group of auxiliary enzymes having the specified enzyme activity pattern enables high production of isopropyl alcohol.

That is, as a result of various studies aiming to improve the efficiency of production of isopropyl alcohol, the invention has found that inactivation of the activity of GntR, which is a negative regulator of gluconate metabolism, improves the efficiency of production of isopropyl alcohol by the *Escherichia coli*.

In addition, it was also found that there are enzymes that affect the improved isopropyl alcohol production capacity achieved by the inactivation of GntR activity. The improved isopropyl alcohol production capacity achieved by the inactivation of GntR is maintained or enhanced, depending on the activity pattern of these enzymes.

As used in the invention, the term "group of auxiliary enzymes" refers to one enzyme, or two or more enzymes, which affect(s) isopropyl alcohol production capacity. Further, the activity of enzymes included in the group of auxiliary enzymes is inactivated, activated or enhanced, and the phrase "enzyme activity pattern of the group of auxiliary enzymes" as used in the invention refers to an enzyme activity pattern of the enzymes that is capable of maintaining or increasing the improved isopropyl alcohol production amount achieved by inactivation of the GntR activity alone, and encompasses one enzyme or a combination of two or more enzymes.

The group of auxiliary enzymes may be a group of enzymes composed only of native enzymes except that an isopropyl alcohol production system is provided, and that the GntR activity is inactivated (in the invention, factors that exhibit no enzyme activity by themselves are also included in the scope of "enzymes", unless specifically indicated to be excluded).

The scope of the isopropyl alcohol-producing *Escherichia coli* described above encompasses, for example:

isopropyl alcohol-producing *Escherichia coli* to which no artificial alteration is made except that an isopropyl alcohol production system exerting the predetermined isopropyl alcohol production capacity is provided, and that GntR was inactivated by gene recombination technology; and isopropyl alcohol-producing *Escherichia coli* to which no artificial alteration is made except that an isopropyl alcohol production system modified to improve isopropyl alcohol production capacity is provided, and that GntR is inactivated by gene recombination technology.

Examples of preferable enzyme activity patterns of the group of auxiliary enzymes include the following patterns:

(1) maintenance of the wild-type activities of glucose-6-phosphate isomerase (Pgi) activity, glucose-6-phosphate 1-dehydrogenase (Zwf) activity and phosphogluconate dehydrogenase (Gnd) activity;

(2) inactivation of glucose-6-phosphate isomerase (Pgi) activity and enhancement of glucose-6-phosphate 1-dehydrogenase (Zwf) activity; and (3) inactivation of glucose-6-phosphate isomerase (Pgi) activity, enhancement of glucose-6-phosphate 1-dehydrogenase (Zwf) activity and inactivation of phosphogluconate dehydrogenase (Gnd) activity.

Among them, the enzyme activity pattern of the group of auxiliary enzymes described in the item (3) is more preferable from the viewpoint of isopropyl alcohol production capacity.

The group of auxiliary enzymes according to the invention and the enzyme activity pattern thereof are not limited to the those described above. Any group of auxiliary enzymes and enzyme activity pattern thereof which include inactivation of the GntR activity, and with which the amount of isopropyl alcohol production amount in the isopropyl alcohol-producing *Escherichia coli* can be increased, are within the scope of the invention. Further, the group of auxiliary enzymes is not necessarily constituted by plural enzymes, and may be constituted by one enzyme.

As used in the invention, the term "inactivation" refers to a condition in which the activity of the factor or enzyme as measured by any existing measurement system is not higher than 1/10 of the activity in the *Escherichia coli* before inactivation, assuming that the activity in the *Escherichia coli* before inactivation is 100.

As used in the invention, the phrase "by gene recombination technology" encompasses any alteration to the base sequence caused by insertion of another DNA into a the base sequence of a native gene, substitution or deletion of a certain site of a gene, or a combination thereof. For example, the alteration may result from a mutation.

In the invention, *Escherichia coli* in which the activity of a factor or enzyme is inactivated refers to a bacterium in which the native activity is impaired by some method applied from outside the bacterial cell to the inside of the bacterial cell. The bacterium can be generated by, for example, disrupting a gene encoding the protein or enzyme (gene disruption).

Examples of the gene disruption in the invention include addition of a mutation to the base sequence of a gene, insertion of another DNA into the base sequence, and deletion of a certain part of a gene, which are carried out with a view to preventing the function of the gene from being performed. As a result of the gene disruption, for example, the gene becomes unable to be transcribed into mRNA, and the structural gene ceases to be translated. Alternatively, due to incompleteness of transcribed mRNA, mutation or deletion appears in the amino acid sequence of the translated structural protein, and thus the intrinsic functions of the structural protein becomes unable to be performed.

Any method may be employed for the preparation of a gene disruptant as long as a disruptant in which the enzyme or protein is not expressed is obtained thereby. Various gene disruption methods (natural breeding, addition of a mutagenic agent, ultraviolet irradiation, exposure to radiation, random mutagenesis, transposon, site-directed gene disruption) have been reported. Gene disruption by homologous recombination is preferable due to its capability of disruption of only a specified gene. Techniques by homologous recombination are described in J. Bacteriol., 161, 1219-1221 (1985), J. Bacteriol., 177, 1511-1519 (1995) and Proc. Natl. Acad. Sci. U.S.A, 97, 6640-6645 (2000), and those skilled in the art can readily carry out the gene disruption using these methods and applications thereof.

In the invention, the "enhancement" of "activity" broadly means that an enzyme activity in isopropyl alcohol-producing *Escherichia coli* becomes higher after enhancement as compared to the enzyme activity before enhancement.

Methods for the enhancement are not particularly restricted as long as the activity of an enzyme possessed by isopropyl alcohol-producing *Escherichia coli* is enhanced. Examples thereof include enhancement by an enzyme gene introduced from outside the bacterial cell, enhancement by augmented expression of an enzyme gene inside the bacterial cell, and a combination thereof.

Examples of enhancement by an enzyme gene introduced from outside the bacterial cell include, specifically: introducing a gene encoding an enzyme having higher activity than the enzyme of the host from outside the bacterial cell of the host bacterium into inside the bacterial cell, thereby adding the enzyme activity of the introduced enzyme gene; substituting the introduced enzyme activity for an intrinsic enzyme activity that the host originally possess; increasing the copy number of an enzyme gene of the host or an enzyme gene introduced from outside the bacterial cell to 2 or more; and any combination thereof.

Examples of enhancement by augmented expression of an enzyme gene inside the bacterial cell include, specifically: introducing a base sequence that enhances the expression of an enzyme gene from outside the bacterial cell of the host bacterium into inside the bacterial cell; substituting another promoter for the promoter of an enzyme gene that the host bacterium possesses on its genome, thereby enhancing the expression of the enzyme gene; and any combination thereof.

In the invention, the term "host" means *Escherichia coli* that will become the isopropyl alcohol-producing *Escherichia coli* according to the invention as a result of the introduction of one or more genes from outside the cell thereof.

The invention is described below.

GntR in the invention refers to a transcription factor that negatively regulates an operon participating in gluconate metabolism via the Entner-Doudoroff pathway, and is a generic name for GntR transcriptional repressor that suppresses the functions of two gene groups (GntI and GntII), which are responsible for the uptake and metabolism of gluconic acid.

Glucose-6-phosphate isomerase (Pgi) in the invention refers to a generic name of enzymes which are classified as enzyme code number 5.3.1.9 based on the report of the Enzyme Commission of the International Union of Biochemistry (I.U.B), and which catalyze a reaction of producing D-fructose-6-phosphate from D-glucose-6-phosphate.

Glucose-6-phosphate 1-dehydrogenase (Zwf) in the invention refers to a generic name of enzymes which are classified as enzyme code number 1.1.1.49 based on the report of the Enzyme Commission of the International Union of Biochemistry (I.U.B), and which catalyze a reaction of producing D-glucono-1,5-lactone 6-phosphate from) D-glucose-6-phosphate.

Examples of such enzymes include those derived from bacteria of the genus *Deinococcus* such as *Deinococcus radiophihis*, bacteria of the genus *Aspergillus* such as *Aspergillus niger* and *Aspergillus aculeatus*, bacteria of the genus *Acetobacter* such as *Acetobacter hansenii*, bacteria of the genus *Thermotoga* such as *Thermotoga maritinia*, bacteria of the genus *Cryptococcus* such as *Cryptococcus neoformans*, bacteria of the genus *Dictyostelium* such as *Dictyostelium discoideum*, the genus *Pseudomonas* such as *Pseudomonas fluorescens* and *Pseudomonas aeruginosa*, the genus *Saccharomyces* such as *Saccharomyces cerevisiae*, bacteria of the genus *Bacillus* such as *Bacillus megaterium*, and bacteria of the genus *Escherichia* such as *Escherichia coli*.

As glucose-6-phosphate 1-dehydrogenase (Zwf) gene used in the invention, a DNA having the base sequence of a gene encoding a glucose-6-phosphate 1-dehydrogenase obtained from any of the enzyme-origin organisms described above, or a synthetic DNA sequence that is synthesized based on a known base sequence of the gene, may be utilized. Preferable examples include a DNA having the base sequence of a gene derived from a bacterium of the genus *Deinococcus* such as *Deinococcus radiophilus*, a bacterium of the genus *Aspergillus* such as *Aspergillus niger* or *Aspergillus aculeatus*, a bacterium of the genus *Acetobacter* such as *Acetobacter hansenii*, a bacterium of the genus *Thermotoga* such as *Thermotoga maritima*, a bacterium of the genus *Cryptococcus* such as *Cryptococcus neoformans*, a bacterium of the genus *Dictyostelium* such as *Dictyostelium discoideum*, the genus *Pseudomonas* such as *Pseudomonas fluorescens* or *Pseudomonas aeruginosa*, the genus *Saccharomyces* such as *Saccharomyces cerevisiae*, a bacterium of the genus *Bacillus* such as *Bacillus megaterium*, or a bacterium of the genus *Escherichia* such as *Escherichia coli*. A DNA having the base sequence of a gene derived from a prokaryote such as a bacterium of the genus *Deinococcus*, a bacterium of the genus *Aspergillus*, a bacterium of the genus *Acetobacter*, a bacterium of the genus *Thermotoga*, a bacterium of the genus *Pseudomonas*, a bacterium of the genus *Bacillus* or a bacterium of the genus *Escherichia* is more preferable, and a DNA having the base sequence of a gene derived from *Escherichia coli* is particular preferable.

Phosphogluconate dehydrogenase (Gnd) in the invention refers to a generic name of enzymes which are classified as enzyme code number 1.1.1.44 based on the report of the Enzyme Commission of the International Union of Biochemistry (I.U.B), and which catalyze a reaction of producing D-ribulose-5-phosphate and $CO_2$ from 6-phospho-D-gluconate.

The isopropyl alcohol-producing *Escherichia coli* according to the invention is *Escherichia coli* having an isopropyl alcohol production system, and has isopropyl alcohol production capacity that is introduced or altered by a gene recombination technology. The isopropyl alcohol production system may be any system that enables the target *Escherichia coli* to produce isopropyl alcohol.

A preferable example is enhancement of an enzyme activity involved in isopropyl alcohol production. In the isopropyl alcohol-producing *Escherichia coli* according to the invention, four types of enzyme activities of acetoacetate decarboxylase activity, isopropyl alcohol dehydrogenase activity, CoA transferase activity and the above-described thiolase activity are imparted from outside the bacterial cell, or expression of the activities are enhanced in the bacterial cell, or, more preferably, both the impartment and the enhancement are carried out.

In the invention, thiolase refers to a generic name of enzymes which are classified as enzyme code number: 2.3.1.9 based on the report of the Enzyme Commission of the International Union of Biochemistry (I.U.B), and which catalyze a reaction of producing acetoacetyl CoA from acetyl CoA.

Examples of the enzyme include those derived from bacteria of the genus *Clostridium* such as *Clostridium acetobutylicum* and *Clostridium beijerinckii*, bacteria of the genus *Escherichia* such as *Escherichia coli*, bacteria of the species *Halobacterium*, bacteria of the genus *Zoogloea* such as *Zoogloea ramigera*, bacteria of the species *Rhizobium*, bacteria of the genus of *Bradyrhizobium* such as *Bradyrhizobium japonicum*, bacteria of the genus *Candida* such as *Candida tropicalis*, bacteria of the genus *Caulobacter* such as *Caulobacter crescentus*, bacteria of the genus *Streptomyces* such as *Streptomyces collinus*, and bacteria of the genus *Enterococcus* such as *Enterococcus faecalis*.

As a gene of the thiolase to be used in the invention, a DNA having the base sequence of a gene encoding a thiolase obtained from any of the above-listed enzyme origin organisms, or a synthesized DNA sequence that is synthesized based on a known base sequence of the gene, may be used. Preferable examples include a DNA having the base sequence of a gene derived from a bacterium of the genus *Clostridium* such as *Clostridium acetobutylicum* or *Clostridium beijerinckii*, a bacterium of the genus *Escherichia* such as *Escherichia coli*, a bacterium of the species *Halobacterium*, a bacterium of the genus *Zoogloea* such as *Zoogloea ramigera*, a bacterium of the species *Rhizobium*, a bacterium of the genus *Bradyrhizobium* such as *Bradyrhizobium japonicum*, a bacterium of the genus *Candida* such as *Candida tropicalis*, a bacterium of the genus *Caulobacter* such as *Caulobacter crescentus*, a bacterium of the genus *Streptomyces* such as *Streptomyces collinus*, or a bacterium of the genus *Enterococcus* such as *Enterococcus faecalis*. More preferable examples include a DNA having the base sequence of a gene derived from a procaryote such as a bacterium of the genus *Clostridium* or a bacterium of the genus *Escherichia*, and a DNA having the base sequence of a gene derived from *Clostridium acetobutylicum* or *Escherichia coli* is particularly preferable.

In the invention, acetoacetate decarboxylase refers to a generic name of enzymes which are classified as enzyme code number: 4.1.1.4 based on the report of the Enzyme Commission of the International Union of Biochemistry (I.U.B), and which catalyze a reaction of producing acetone from acetoacetate.

Examples of the enzymes include those derived from bacteria of the genus *Clostridium*, such as *Clostridium acetobutylicum* and *Clostridium beijerinckii*, and bacteria of the genus *Bacillus* such as *Bacillus polymyxa*.

As a gene of the acetoacetate decarboxylase to be introduced into the host bacterium in the invention, a DNA having the base sequence of a gene encoding an acetoacetate decarboxylase obtained from any of the above-listed enzyme origin organisms, or a synthetic DNA sequence that is synthesized based on a known base sequence of the gene, may be used. Preferable examples include those derived from bacteria of the genus *Clostridium* or bacteria of the genus *Bacillus*. An example is a DNA having the base sequence of a gene derived from *Clostridium acetobutylicum* or *Bacillus polymyxa*. A DNA having the base sequence of a gene derived from *Clostridium acetobutylicum* is particularly preferable.

In the invention, isopropyl alcohol dehydrogenase refers to a generic name of enzymes which are classified as enzyme code number: 1.1.1.80 based on the report of the Enzyme Commission of the International Union of Biochemistry (I.U.B), and which catalyze a reaction of producing isopropyl alcohol from acetone. Examples of the enzyme include those derived from bacteria of the genus *Clostridium*, such as *Clostridium beijerinckii*.

As a gene of the isopropyl alcohol dehydrogenase to be introduced into the host bacterium in the invention, a DNA having the base sequence of a gene encoding an isopropyl alcohol dehydrogenase obtained from any of the above-listed enzyme origin organisms, or a synthetic DNA sequence that is synthesized based on a known base sequence of the gene, may be used. Preferable examples include those derived from bacteria of the genus *Clostridium*, such as a DNA having the base sequence of a gene derived from *Clostridium beijerinckii*.

In the invention, CoA transferase refers to a generic name of enzymes which are classified as enzyme code number: 2.8.3.8 based on the report of the Enzyme Commission of the International Union of Biochemistry (I.U.B), and which catalyze a reaction of producing acetoacetate from acetoacetyl CoA.

Examples of the enzyme include those derived from bacteria of the genus *Clostridium*, such as *Clostridium acetobutylicum* and *Clostridium beijerinckii*, bacteria of the genus *Roseburia*, such as *Roseburia intestinalis*, bacteria of the genus *Faecalibacterium* such as *Faecalibacterium prausnitzii*, bacteria of the genus *Coprococcus, Trypanosoma* such as *Trypanosoma brucei*, and bacteria of the genus *Escherichia* such as *Escherichia coli*.

As a gene of the CoA transferase to be used in the invention, a DNA having the base sequence of a gene encoding a CoA transferase obtained from any of the above-listed enzyme origin organisms, or a synthetic DNA sequence that is synthesized based on a known base sequence of the gene, may be used. Preferable examples include a DNA having the base sequence of a gene derived from a bacterium of the genus *Clostridium* such as *Clostridium acetobutylicum*, a bacterium of the genus *Roseburia* such as *Roseburia intestinalis*, a bacterium of the genus *Faecalibacterium* such as *Faecalibacterium prausnitzii*, a bacterium of the genus *Coprococcus, Trypanosoma* such as *Trypanosoma brucei*, or a bacterium of the genus *Escherichia* such as *Escherichia coli*. More preferable examples include those derived from a bacterium of the genus *Clostridium* or a bacterium of the genus *Escherichia*, and a DNA having the base sequence of a gene derived from *Clostridium acetobutylicum* or *Escherichia coli* is particularly preferable.

From the viewpoint of enzyme activity, it is preferable that each of the four kinds of enzyme is an enzyme derived from at least one selected from the group consisting of a bacterium of the genus *Clostridium*, a bacterium of the genus *Bacillus*, and a bacterium of the genus *Escherichia*. In particular, a case in which the acetoacetate decarboxylase and the isopropyl alcohol dehydrogenase are derived from a bacterium or bacteria of the genus *Clostridium*, and in which the CoA transferase activity and the thiolase activity are derived from a bacterium or bacteria of the genus *Escherichia*, is more preferable.

In particular, from the viewpoint of the enzyme activity, it is preferable that each of the four kinds of enzyme in the invention comes from any of *Clostridium acetobutylicum*, *Clostridium beijerinckii*, or *Escherichia coli*. A case in which the acetoacetate decarboxylase is an enzyme derived from *Clostridium acetobutylicum*, and in which each of the CoA transferase and the thiolase is an enzyme derived from *Clostridium acetobutylicum* or *Escherichia coli*, and in which the isopropyl alcohol dehydrogenase is an enzyme derived from *Clostridium beijerinckii*, is more preferable. In regard to the four kinds of enzyme, a case in which the acetoacetate decarboxylase activity is derived from *Clostridium acetobutylicum*, and in which the isopropyl alcohol dehydrogenase activity is derived from *Clostridium beijerinckii*, and in which the CoA transferase activity and the thiolase activity are derived from *Escherichia coli*, is particularly preferable from the viewpoint of the enzyme activity.

Each of the activities of these enzymes in the invention may be an activity introduced from outside the bacterial cell into inside the bacterial cell, or an activity obtained by high expression of the enzyme gene that the host bacterium possesses on its genome via enhancement of the promoter activity for the enzyme gene or replacement of the promoter with another promoter.

Introduction of the enzyme activity can be carried out by, for example, introducing a gene encoding the enzyme from outside the bacterial cell of the host bacterium into inside the bacterial cell using a gene recombination technology. Here, the enzyme gene to be introduced may be derived from either the same species as that of the host cell or a different species from that of the host cell. Methods for preparation of a genomic DNA necessary to introduce a gene from outside the bacterial cell into inside the bacterial cell, cutting and ligation of DNA, transformation, PCR (Polymerase Chain Reaction), the design and synthesis of oligonucleotides to be used as primers, etc. may be carried out by usual methods well known to those skilled in the art. These methods are described in Sambrook, J., et al., "Molecular Cloning A Laboratory Manual, Second Edition", Cold Spring Harbor Laboratory Press, (1989) etc.

In the invention, Escherichia coli in which an enzyme activity is enhanced refers to Escherichia coli in which the enzyme activity is enhanced by some method. Such Escherichia coli can be prepared using, for example, a method in which a gene encoding the enzyme or protein is introduced from outside the bacterial cell to inside the bacterial cell using a plasmid and a gene recombination technology similar to those described above, a method in which high expression of an enzyme gene that the host Escherichia coli possesses on its genome is achieved by enhancement of the promoter activity for the enzyme gene or replacement of the promoter with another promoter.

The gene promoter in the invention may be any promoter that is capable of controlling the expression of any of the genes described above. The gene promoter is preferably a powerful promoter which constitutively works in the microorganism, and which is not susceptible to repression of expression even in the presence of glucose. Specific examples thereof include the promoter of glyceraldehyde-3-phosphate dehydrogenase (hereinafter sometimes referred to as "GAPDH") or the promoter of serine hydroxymethyl transferase.

The promoter in the present invention means a region to which an RNA polymerase having a sigma factor binds to start transcription. For example, a GAPDH promoter derived from Escherichia coli is described at Base Nos. 397-440 in the base sequence information of GenBank accession number X02662.

CoA transferase genes (atoD and atoA) and a thiolase gene each of which is derived from Escherichia coli, form an operon on the genome of Escherichia coli in the order of atop, atoA, and atoB (Journal of Baceteriology Vol. 169 pp 42-52 Lauren Sallus Jenkins, et al.) Therefore, the expression of the CoA transferase genes and the thiolase gene can be simultaneously controlled by modifying the promoter of atop.

In view of the above, when the CoA transferase activity and the thiolase activity are obtained from the genomic genes of the host Escherichia coli, it is preferable to enhance the expression of both enzyme genes by, for example, replacing the promoter responsible for the expression of both enzyme genes by another promoter, from the viewpoint of obtaining sufficient isopropyl alcohol production ability. Examples of the promoter to be used in order to enhance the expression of the CoA transferase activity and the thiolase activity include the above-described Escherichia coli-derived GAPDH promoter.

In the present invention, examples of isopropyl alcohol-producing Escherichia coli having an isopropyl alcohol production system include the pIPA/B variant or the pIaaa/B variant described in WO 2009/008377. The scope of such Escherichia coli includes a variant in which, from among enzymes involved in the production of isopropyl alcohol, enhancement of CoA transferase activity and thiolase activity is carried out by enhancement of the expression of the respective genes on the genome of the Escherichia coli, and in which enhancement of isopropyl alcohol dehydrogenase activity and acetoacetate decarboxylase activity is carried out by enhanced expression of the respective genes using a plasmid or plasmids (sometimes referred to as "pIa/B::atoDAB variant").

In the invention, inactivated GntR activity is preferably included from the viewpoint of more effectively improving the efficiency of isopropyl alcohol production. It is more preferable that inactivated glucose-6-phosphate isomerase (Pgi) activity and enhanced glucose-6-phosphate 1-dehydrogenase (Zwf) activity are included in addition to the inactivated GntR. It is most preferable that inactivated GntR activity, inactivated glucose-6-phosphate isomerase (Pgi) activity, inactivated phosphogluconate dehydrogenase (Gnd) activity and enhanced glucose-6-phosphate 1-dehydrogenase (Zwf) activity are included. These combinations enable drastic improvement of the efficiency of isopropyl alcohol production, as compared with other combinations of factors or enzymes.

A preferable aspect of the isopropyl alcohol-producing Escherichia coli according to the invention is a variant obtained by inactivating the GntR activity of the pIPA/B variant, the pIaaa/B variant or the pIa/B::atoDAB variant.

A more preferable aspect thereof is a variant obtained by inactivating the GntR activity and the glucose-6-phosphate isomerase (Pgi) activity of the pIPA/B variant, the pIaaa/B variant or the pIa/B::atoDAB variant, and enhancing the glucose-6-phosphate 1-dehydrogenase (Zwf) activity thereof.

A particularly preferable aspect is a variant obtained by inactivating the GntR activity, the glucose-6-phosphate isomerase (Pgi) activity, and the phosphogluconate dehydrogenase (Gnd) activity of the pIPA/B variant, the pIaaa/B variant or the pIa/B::atoDAB variant, and enhancing the glucose-6-phosphate-dehydrogenase (Zwf) activity thereof.

Further, genes encoding sucrose assimilation enzymes may be introduced into the isopropyl alcohol-producing Escherichia coli according to the invention. The introduction of such genes enables production of isopropyl alcohol from sucrose.

The genes encoding sucrose assimilation enzymes include genes encoding enzymes involved in the PTS system and the non-PTS system among sucrose assimilation pathways of microorganisms.

Specifically, examples of genes encoding enzymes involved in the sucrose PTS include genes encoding ScrA (which incorporates sucrose), ScrY (which phosphorylates sucrose), ScrB (which degrades sucrose inside the microorganism), ScrR (which regulates the expression of genes encoding ScrA, Y, and B), and ScrK (which phosphorylates fructose).

Further, a group of sucrose non-PTS genes that encodes the enzymes involved in the sucrose non-PTS is, specifically, a group of genes composed of genes encoding CscB (sucrose permease, which incorporates sucrose), CscA (sucrose hydrolase, which degrades sucrose inside the microorganism), CscK (fructokinase, which phosphorylates fructose), and CscR (repressor protein, which regulates the expression of genes encoding CscB, A, and K).

Among them, examples of a sucrose assimilation enzyme gene to be introduced into the isopropyl alcohol-producing

*Escherichia coli* according to the invention include genes encoding enzymes involved in the non-PTS system, and, especially, genes encoding a combination of one or more enzymes including at least CscA. Examples thereof include cscA alone, a combination of cscA and cscK, a combination of cscA and cscB, a combination of cscA and cscR, a combination of cscA, cscR and cscK, and a combination of cscA, cscR and cscB. In particular, it is possible to choose to introduce only a CscA-encoding gene from the viewpoint of efficient production of isopropyl alcohol.

As a gene of the sucrose hydrolase (invertase, CscA), a DNA having the base sequence of a gene encoding a sucrose hydrolase (invertase, CscA) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of a gene derived from an *Escherichia coli* O157 strain. A DNA having the base sequence of a gene derived from an *Escherichia coli* O157 strain is particularly preferable. It is preferable that a signal sequence for transferring cscA to the periplasm of the bacterial cell has been added to cscA.

As a gene of the repressor protein (CscR), a DNA having the base sequence of a gene encoding a repressor protein (CscR) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of a gene derived from an *Escherichia coli* O157 strain. The DNA having the base sequence of a gene derived from an *Escherichia coli* O157 strain is particularly preferable.

As a gene of the fructokinase (CscK), a DNA having the base sequence of a gene encoding a fructokinase (CscK) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of a gene derived from an *Escherichia coli* O157 strain. The DNA having the base sequence of a gene derived from an *Escherichia coli* O157 strain is particularly preferable.

As a gene of the sucrose permease (CscB), a DNA having the base sequence of a gene encoding a sucrose permease (CscB) obtained from an organism possessing the enzyme, or a synthetic DNA sequence that is synthesized based on a known base sequence of the gene, may be used. Preferable examples include those derived from bacteria of the genus *Erwinia*, bacteria of the genus *Proteus*, bacteria of the genus *Vibrio*, bacteria of the genus *Agrobacterium*, bacteria of the genus *Rhizobium*, bacteria of the genus *Staphylococcus*, bacteria of the genus *Bifidobacterium*, and bacteria of the genus *Escherichia*. An example is a DNA having the base sequence of a gene derived from an *Escherichia coli* O157 strain. The DNA having the base sequence of a gene derived from an *Escherichia coli* O157 strain is particularly preferable.

In the isopropyl alcohol-producing *Escherichia coli* according to the invention, the activity of an enzyme of the isopropyl alcohol production system, preferably the activity of at least one of isopropyl alcohol dehydrogenase or acetoacetate dehydrogenase among the enzymes of the isopropyl alcohol production system, may be derived from a gene introduced as a modified gene.

As used in the invention, the phrase "modified gene" encompasses any product obtained by subjecting the base sequence of the enzyme gene to modification, such as deletion, substitution or addition. Specifically, examples thereof include a product in which modification is made only to codons of the base sequence of the enzyme gene and in which the amino acid sequence synthesized based on the base sequence modified only for codons is not changed, and a product in which modification is made only to the promoter region of an enzyme gene and in which the amino acid sequence synthesized based on the base sequence modified only at the promoter region is not changed.

The enzyme gene to be modified may be an innate gene of the host or an enzyme gene derived from a microorganism of a different species.

Further, only an enzyme gene encoding isopropyl alcohol dehydrogenase or only an acetoacetate dehydrogenase enzyme gene may be genetically modified, or both genes may be genetically modified at the same time.

The modified gene may have any modification as long as the gene modification to any of the enzyme genes described above results in enhancement of the capacity to produce a target substance through provision of the enzyme activity of a corresponding enzyme to a host or through enhancement of the enzyme activity.

The modified gene is preferably a modified gene of which the employed codons have been modified in accordance with the frequency of the usage of the codons in *Escherichia coli*. Such a modified gene enables an increase in the efficiency of isopropyl alcohol production.

As used in the invention, the phrase "modify the employed codons" means modification to codons, which are sequences of base triplets corresponding to respective amino acids, on the base sequence encoding and defining an amino acid sequence. As used in the invention, the expression "codon modification" means modification to only the base sequence without alteration to the amino acid sequence.

The modified gene of isopropyl alcohol dehydrogenase preferably has a base sequence represented by SEQ ID NO: 40. The modified gene of acetoacetate dehydrogenase preferably has a base sequence represented by SEQ ID NO: 43. The activity of each of isopropyl alcohol dehydrogenase and acetoacetate dehydrogenase can preferably be enhanced by using the modified genes.

In the present invention, *Escherichia coli* means *Escherichia coli* that can be made to have the ability to produce isopropyl alcohol from a plant-derived raw material by using a certain means, regardless of whether or not the *Escherichia coli* originally has the ability to produce isopropyl alcohol from a plant-derived raw material.

Here, the *Escherichia coli* which is to be subjected to genetic recombination may be *Escherichia coli* that does not have isopropyl alcohol production capacity, and may be any *Escherichia coli* that allows the introduction or modification of the respective genes.

The *Escherichia coli* may more preferably be *Escherichia coli* to which isopropyl alcohol production ability has been imparted in advance. By using such *Escherichia* isopropyl alcohol can more efficiently be produced.

An example of such isopropyl alcohol-producing *Escherichia coli* is an isopropyl alcohol-producing *Escherichia coli* to which acetoacetate decarboxylase activity, isopropyl alcohol dehydrogenase activity, CoA transferase activity, and thiolase activity have been imparted so as to be capable of producing isopropyl alcohol from a plant-derived raw material, and which is described in, for example, WO 2009/008377 pamphlet.

A method of producing isopropyl alcohol according to the invention includes producing isopropyl alcohol from a plant-derived raw material using the above-described isopropyl alcohol-producing *Escherichia coli*, and specifically includes culturing the isopropyl alcohol-producing *Escherichia coli* in a state in which the isopropyl alcohol-producing *Escherichia coli* contacts with a plant-derived raw material (hereinafter, culture process), and collecting isopropyl alcohol obtained by the contact (hereinafter, collection process).

The plant-derived raw material to be used in the method of producing isopropyl alcohol is a carbon source obtained from a plant, and is not restricted as long as it is a plant-derived raw material. In the invention, the plant-derived raw material refers to organs such as roots, stalks, stems, branches, leaves, flowers, and seeds, plant bodies including the plant organs, and decomposition products of the plant organs, and further encompasses carbon sources that can be used as carbon sources by microorganisms during cultivation from among carbon sources obtained from the plant bodies, the plant organs and decomposition products thereof.

The carbon sources included in such plant-derived raw materials generally include sugars such as starch, sucrose, glucose, fructose, xylose, and arabinose, or herbaceous and ligneous plant decomposition products or cellulose hydrolysates, each of which contains the above ingredients in large amounts, and combinations thereof. The carbon sources in the invention may further include vegetable oil-derived glycerin and fatty acids.

Preferable examples of the plant-derived raw material in the invention include agricultural products such as grain, corn, rice, wheat, soybean, sugarcane, beet, cotton, and the like, or combinations thereof. The form thereof as the raw material is not specifically limited, and may be a crude product, squeezed juice, a crushed product, or the like. Alternatively, the plant-derived raw material may be in a form that consists only of the carbon source described above.

In the culture process, the contact between the isopropyl alcohol-producing *Escherichia coli* and a plant-derived raw material is generally made by culturing the isopropyl alcohol-producing *Escherichia coli* in a culture medium containing the plant-derived raw material.

The density of contact between the plant-derived raw material and the isopropyl alcohol-producing *Escherichia coli* may be varied depending on the activity of the isopropyl alcohol-producing *Escherichia coli*. In general, the concentration of the plant-derived raw material in the culture medium may be such that the initial sugar concentration in terms of glucose may be set to be 20% by mass or lower relative to the total mass of the mixture. From the viewpoint of sugar tolerance of *Escherichia coli*, the initial sugar concentration is preferably set to be 15% by mass or lower. Other components may be added in usual addition amounts for microorganism culture media, without particular limitation.

The content of the isopropyl alcohol-producing *Escherichia coli* in the culture medium may be varied with the kind and activity of the *Escherichia coli*, and the amount of a preculture bacterial liquid (OD 660 nm=4 to 8) to be added when starting cultivation may generally be set to be from 0.1% by mass to 30% by mass relative to the culture liquid, and is preferably set to be from 1% by mass to 10% by mass relative to the culture liquid from the viewpoint of controlling culture conditions.

The culture medium to be used for culture of the isopropyl alcohol-producing *Escherichia coli* may be any usually-employed culture medium that includes a carbon source, a nitrogen source, inorganic ions, and organic trace elements, nucleic acids, vitamins, etc. required by microorganisms to produce lactic acid, without particular limitation.

Culture conditions for culturing in the invention are not particularly restricted, and culturing may be carried out, for example, under aerobic conditions at an appropriately controlled pH and temperature within a range of from pH 4 to 9, preferably from pH 6 to 8, and within a range of from 20° C. to 50° C., preferably from 25° C. to 42° C.

The aeration volume of gas into the mixture described above is not particularly restricted. When air alone is used as the gas, the aeration volume is generally from 0.02 vvm to 2.0 vvm (vvm; aeration volume [mL]/liquid volume [mL]/time [min]), and, from the viewpoint of suppressing physical damages to *Escherichia coli*, the aeration is preferably carried out at 0.1 vvm to 1.5 vvm.

The culture process may be continued from the beginning of culturing until the plant-derived raw material in the mixture is exhausted, or until the activity of the isopropyl alcohol-producing *Escherichia coli* disappears. The duration of the culture process may be varied with the number and activity of the isopropyl alcohol-producing *Escherichia coli* in the mixture and the amount of the plant-derived raw material. In general, the duration may be at least one hour, and preferably at least four hours. The duration of culturing may be unlimitedly continued by anew addition of the plant-derived raw material or the isopropyl alcohol-producing *Escherichia coli*. However, from the viewpoint of process efficiency, the duration may generally be set to 5 days or less, preferably 72 hours or less. With regard to other conditions, conditions employed for usual cultivation may be applied as they are.

Methods for collecting isopropyl alcohol accumulated in the culture medium are not particularly restricted. For example, a method may be employed which includes removing bacterial cells from the culture liquid by, for example, centrifugal separation, and thereafter separating isopropyl alcohol using a usual separation method such as distillation or membrane separation.

The method of producing isopropyl alcohol according to the invention may further include a preculture process before the culture process for producing isopropyl alcohol, with a view to achieving an appropriate cell number or appropriate activated state of the isopropyl alcohol-producing *Escherichia coli* to be used. The preculture process may be any cultivation conducted under usually-employed culture conditions suitable for the type of isopropyl alcohol-producing bacterium employed.

The method of producing isopropyl alcohol according to the invention preferably includes a culture process in which the isopropyl alcohol-producing *Escherichia coli* is cultured while gas is supplied into the mixture containing the isopropyl alcohol-producing bacterium and the plant-derived raw material; and a collection process in which isopropyl alcohol produced by the culturing is separated and collected from the mixture.

According to this method, the productive *Escherichia coli* is cultured while gas is supplied into the mixture (aeration culture). In this aeration culture, isopropyl alcohol produced is released into the mixture, and evaporated from the mixture.

As a result, the isopropyl alcohol produced can be easily separated from the mixture. Further, since the isopropyl alcohol produced is continuously separated from the mixture, an increase in the concentration of isopropyl alcohol in the mixture can be regulated. Therefore, it is not necessary to pay particular attention to the tolerance of the isopropyl alcohol-producing *Escherichia coli* against isopropyl alcohol.

The mixture in this method may be mainly composed of a basic medium generally used in culture of *Escherichia coli*. With regard to culture conditions, those described above shall apply as they are.

In the collection process, isopropyl alcohol produced in the culture process and separated from the mixture is collected. The collection method may be any method capable of collecting isopropyl alcohol in the gaseous or droplet state evaporated from the mixture by usual cultivation. Examples of such a method include a method of collecting into a collection member such as a commonly-employed airtight container. In particular, the method preferably includes contacting a trap solution for trapping isopropyl alcohol with isopropyl alcohol separated from the mixture, from the viewpoint of collecting only isopropyl alcohol with high purity.

In the present method, isopropyl alcohol can be collected in a state in which isopropyl alcohol is dissolved in a trap solution or the mixture. Examples of such a collation method include a method described in WO 2009/008377 pamphlet. The isopropyl alcohol collected can be confirmed using a usual detection means such as HPLC. The isopropyl alcohol collected may be further purified, if necessary. Examples of the purification method include distillation, etc.

In a case in which the isopropyl alcohol collected is in the state of aqueous solution, the present isopropyl alcohol production method may further include a dehydration process in addition to the collection process. The dehydration of isopropyl alcohol can be carried out using an ordinary method.

An example of apparatuses applicable to the isopropyl alcohol production method in which isopropyl alcohol can be collected in the state of being dissolved in the trap solution or the mixture is the production apparatus shown in FIG. 1 of WO 2009/008377 pamphlet.

In the production apparatus, an injection pipe for injecting a gas from outside the apparatus is connected to a culture tank that contains a culture medium including an isopropyl alcohol-producing bacterium and a plant-derived raw material, thereby enabling aeration to the culture medium.

A trap tank that contains a trap solution as the trap solution is connected to the culture tank via a connection pipe. A gas or liquid that has moved to the trap tank contacts the trap solution, and bubbling occurs.

As a result, isopropyl alcohol, which has been produced in the culture tank by cultivation under aeration, is evaporated due to aeration, and thus easily separated from the culture medium, and is trapped in the trap solution in the trap tank. As a result, isopropyl alcohol can be produced in a more purified state in a simple and continuous manner.

The isopropyl alcohol production method according to the invention enables high production of isopropyl alcohol, and the production amount usually obtained by employing the method according to the invention is greater than the production amounts usually obtained by employing similar methods to which the invention is not applied. Although the productivity varies with the conditions of the production method and the state of isopropyl alcohol-producing *Escherichia coli* to be used, a productivity of from 50 to 100 g/L/72 hr, preferably from 55 to 80 g/L/72 hr, can be achieved.

As explained above, the isopropyl alcohol-producing *Escherichia coli* according to the invention is capable of high production of isopropyl alcohol. Therefore, for example, 75 g/L or more isopropyl alcohol can be accumulated after culturing for 72 hours in the case of isopropyl alcohol production using the *Escherichia coli* catalyst according to the invention, whereby much higher productivity than that achieved by conventional catalysts can be obtained.

In the isopropyl alcohol-producing *Escherichia coli* according to the invention, acetone, which is a precursor of isopropyl alcohol, is produced at the same time. The acetone obtained is preferably converted into isopropyl alcohol by using a known method (for example, a method described in Japanese Patent Publication No. 2786272) after purification thereof using a known method. This further increases the efficiency of conversion from sugar as a raw material to isopropyl alcohol.

The acetone production method according to the invention is an acetone production method including:

obtaining isopropyl alcohol from a plant-derived raw material using the isopropyl alcohol-producing *Escherichia coli* (hereinafter, refer to as isopropyl alcohol production process); and contacting the obtained isopropyl alcohol with a complex oxide as a catalyst that includes zinc oxide and at least one oxide containing a Group 4 element, and that is prepared by coprecipitation (hereinafter refer to as acetone production process).

The isopropyl alcohol obtained using the isopropyl alcohol-producing *Escherichia coli* is brought into contact with the complex oxide prepared by coprecipitation, whereby a dehydrogenation reaction occurs, and acetone is produced from isopropyl alcohol. In this manner, isopropyl alcohol produced using the isopropyl alcohol-producing *Escherichia coli* can be effectively utilized to realize efficient substance production.

With regard to the isopropyl alcohol-producing *Escherichia coli*, the plant-derived raw material, the conditions of isopropyl alcohol production, etc. employed in the isopropyl alcohol production process, those described above for the production of isopropyl alcohol shall apply as they are.

In the acetone production process, a complex oxide that includes zinc oxide and at least one oxide containing a Group 4 element, and that is prepared by coprecipitation is used as a catalyst.

A Group 4 element means an element of Group 4 of the periodic table, and examples thereof include titanium, zirconium, hafnium, etc. Zirconium is preferable from the viewpoint of highly selective acetone production.

Examples of complex oxides that can be used as a catalyst include $ZnO:ZrO_2$, $ZnO:TiO_2$, $CuO:ZnO:Al_2O_3$, etc. $ZnO:ZrO_2$ is preferable in terms of catalytic activity and acetone selectivity.

The ratio of zinc oxide to the at least one oxide containing a Group 4 element is not particularly restricted, and is preferably from 50:50 to 99:1 from the viewpoint of catalytic activity and acetone selectivity, and more preferably from 65:35 to 95:5. When the proportion of zinc oxide is 50 or higher, a higher catalytic activity can be exhibited. When the proportion of zinc oxide is 99 or lower, a higher acetone selectivity can be exhibited. Therefore, a ratio within the above range is preferable.

The complex oxide is prepared by coprecipitation. Since the complex oxide that can be used as a catalyst is prepared by coprecipitation, the complex oxide has an advantage such as uniformity of the catalyst composition or ease of control over the preparation of catalyst.

Coprecipitation is a preparation method commonly employed as a method for the production of a multicomponent complex oxide, and addition of a precipitant such as an alkaline aqueous solution to a mixed aqueous solution of two or more types of metal salts allows uniform precipitation of the complex oxide as a solid.

In a specific method for preparing the catalyst, an aqueous solution of a water-soluble zinc salt such as zinc nitrate and an aqueous solution of a water-soluble zirconium salt such as zirconium nitrate are mixed so as to attain a desired metal oxide composition. This aqueous solution is dropwise added onto an alkaline aqueous solution such as sodium carbonate for alkalification, so as to precipitate a solid in the form of a hydroxide. The generated precipitate is filtered, washed with water and dried, and thereafter calcinated, as a result of which the catalyst is produced.

The amount of catalyst used when practicing the invention is not particularly restricted. For example, when a reaction is carried out using a fixed bed flow reactor, the value obtained by dividing the amount (mass) of the raw material (isopropyl alcohol) supplied per hour by the mass of the catalyst, —WHSV— is preferably in a range of from 0.01 to 200/h, and more preferably in a range of from 0.02 to 100/h.

The dehydrogenation reaction in the invention may be carried out in a reaction manner such as a batch manner or a continuous manner. In the case of the continuous manner, raw materials are, for example, flowed through a tubular reactor filled with a catalyst, and reaction products coming out of the reactor are collected.

The reaction temperature for carrying out the dehydrogenation reaction may usually be from 100° C. to 500° C., preferably from 150° C. to 450° C., and further preferably from 200° C. to 400° C. There are a relationship of equilibrium between acetone, isopropyl alcohol and hydrogen. A higher reaction temperature results in a higher acetone composition at equilibrium. Therefore, a reaction temperature of 100° C. or higher is preferable since isopropyl alcohol does not remain in a large amount at such a temperature. A reaction temperature of 500° C. or lower is preferable since undesired side reactions do not increase at such a temperature. The reaction pressure is not particularly restricted. Although the reaction pressure depends on the reaction temperature, the reaction pressure is preferably set to be from 0.1 MPa to 1.0 MPa.

After the reaction product is collected, purification, etc. may additionally be carried out, as appropriate, in accordance with the necessity. With regard to the acetone purification method, etc., purification methods known or well-known in the art may be applied.

The propylene production method according to the invention includes:

obtaining acetone-containing isopropyl alcohol from a plant-derived raw material using the isopropyl alcohol-producing *Escherichia coli* (hereinafter referred to as "isopropyl alcohol production process"); and allowing acetone and hydrogen to react with each other in the presence of, as catalysts, a Cu-containing hydrogenation catalyst and a solid acidic substance in a reaction temperature range of from 50 to 300° C. using the obtained acetone-containing isopropyl alcohol (hereinafter referred to as "catalytic reaction process"). In the present specification, the Cu-containing hydrogenation catalyst is hereinafter also referred to simply as "hydrogenation catalyst."

In the propylene production method, the isopropyl alcohol obtained by the isopropyl alcohol-producing *Escherichia coli* is dehydrated by the solid acidic substance to yield propylene and water.

With regard to the isopropyl alcohol-producing *Escherichia coli*, the plant-derived raw material, the conditions of isopropyl alcohol production, etc., employed in the isopropyl alcohol production process, those described above for the production of isopropyl alcohol can be applied as they are.

In the catalytic reaction process, acetone and hydrogen are reacted under predetermined conditions using the acetone-containing isopropyl alcohol obtained in the isopropyl alcohol production process as a raw material and using a Cu-containing hydrogenation catalyst and a solid acidic substance.

The hydrogen to be used in the catalytic reaction process may be molecular hydrogen gas, or may be hydrogen derived from a hydrocarbon, such as cyclohexane, that generates hydrogen, depending on the reaction conditions. The amount of hydrogen may be, in principle, any amount that is not less than an amount equimolar to acetone. From the view of separation and collection, the molar amount of hydrogen is preferably from 1 to 10 times that of acetone, and more preferably from 1 to 5 times that of acetone. For example, the amount of hydrogen supplied per unit time relative to the amount of acetone supplied per unit time may be set to be within the range described above. In a case in which a conversion rate of acetone of 100% or lower is desired, the conversion ratio can be achieved by reducing the amount of hydrogen from the amount equimolar to acetone.

In the catalytic reaction process, the supplied hydrogen binds to the oxygen atom of acetone to form water, which can be discharged from a reactor outlet. Further, hydrogen in excess of the amount equimolar to acetone will not essentially be consumed unless unexpected side reactions proceed.

The supply of hydrogen gas to the reactor is usually carried out by continuous supply, but is not particularly limited thereto. With regard to the manner of hydrogen supply, the supply may be intermittent supply which includes supplying hydrogen gas at the initiation of the reaction, thereafter stopping the supply during the reaction, and restarting the supply after a certain period of time. In the case of a liquid phase reaction, hydrogen gas may be supplied by being dissolved in a solvent.

Further, hydrogen can be recovered from the reactor and reused. The recycle process for hydrogen may include, for example: separating the reaction solution and the reaction gas from each other in the posterior part of the reactor using a gas-liquid separator; separating hydrogen gas from the reaction gas using a separation membrane, etc.; and re-supplying the hydrogen gas to the inlet of the reactor. In the case of this recycle process, hydrogen gas collected from the overhead together with low-boiling fraction can be supplied to the reactor. The pressure of hydrogen to be supplied is generally equal to the pressure of the reactor, but may be changed, as appropriate, in accordance with the hydrogen supply method.

When the invention is practiced, the reaction may be carried out in a diluted state obtained by supplying a solvent or gas that is inert to catalysts and starting materials (acetone, isopropyl alcohol and hydrogen) into the reaction system.

The reaction temperature applied in the catalytic reaction process is from 50° C. to 300° C. With a reaction temperature below 50° C., sufficient conversion ratio of acetone or isopropyl alcohol is not obtained. With a reaction temperature above 300° C., unexpected side reactions, polymerization of propylene, etc. occur, as a result of which a sufficient selection ratio for propylene cannot be maintained. From the viewpoint of economic efficiency, the reaction temperature is preferably in a range of from 150° C. to 250° C., and more preferably in a range of from 150 to 200° C.

In a case in which the reaction is carried out, other methods and conditions are not particularly restricted, and, for example, the conditions and methods mentioned below may be employed. The contact of acetone and isopropyl alcohol, which are starting materials, with hydrogen, and the hydrogen supply method, may be any of gas-liquid countercurrent flow or gas-liquid cocurrent flow. The flow directions of liquid and gas may be any of: descending liquid-ascending gas; ascending liquid-descending gas; ascending liquid-ascending gas; and descending liquid-descending gas. Further, the pressure applied is preferably from 0.1 atm to 500 atm and further preferably from 0.5 atm to 100 atm.

Examples of the solid acidic substance include metal oxides such as zeolite, silica, alumina, silica alumina, γ-alumina, titanium oxide, zinc oxide, and zirconium oxide, which are ordinary solid acids. Among these, zeolite is preferable from the viewpoint of high catalytic activity and high selectivity for propylene.

A zeolite that is favorable in view of the molecular sizes of isopropyl alcohol, which is thought to be present as a raw material and an intermediate in the reaction described above, and propylene, which is the target substance, may be chosen as the zeolite to be used.

Zeolites having 10-ring to 12-ring pores are preferable because their molecular sizes are similar to the molecular sizes of isopropyl alcohol and propylene. Examples of zeolites having 10-ring to 12-ring pores include ferrierite, heulandite, ZSM-5, ZSM-11, ZSM-12, NU-87, theta-1, weinebeneite, zeolite-X, zeolite-Y, USY zeolite, mordenite, dealuminated mordenite, β-zeolite, MCM-22, MCM-56, etc. Of these, β-zeolite is preferable.

The composition ratio of silicon to aluminum (silicon/aluminum) in zeolite is preferably in a range of from 2/1 to 200/1 in order to obtain high activity, and particularly preferably in a range of from 5/1 to 100/1 from the viewpoints of activity and heat stability. Further, a so-called isomorphous-substituted zeolite may be used in which aluminum contained in the zeolite framework is replaced by a metal, other than aluminum, such as Ga, Ti, Fe, Mn or B. The zeolite to be used may also be a zeolite modified with metal ions.

The shape of the solid acidic substance is not particularly restricted, and may be any of spherical, cylindrical, extruded and crushed shapes. The particle size thereof is not particularly restricted, either, and the solid acidic substance may be selected from those having sizes in a range of from 0.01 mm to 100 mm, in accordance with the size of the reactor. One solid acidic substance may be used singly, or two or more solid acidic substances may be used.

Examples of the Cu-containing hydrogenation catalyst include those containing metallic Cu, and those containing Cu in the form of metal compounds, etc. Examples of the metal compounds include metal oxide such as CuO and $Cu_2O$, metal chlorides such as $CuCl_2$, etc. The catalyst may be retained on a carrier.

It is preferable that the Cu-containing hydrogenation catalyst further includes at least one element selected from the group consisting of Group 6, Group 12 and Group 13 elements in the periodic table from the viewpoint of obtaining higher selectivity or longer catalyst life. Preferable elements of Group 6 include Cr, Mo, etc., preferable elements of Group 12 include Zn, etc., and preferable elements of Group 13 include Al, In, etc. Examples of such a hydrogenation catalyst include a copper-based catalyst such as copper-chrome, Raney copper, and copper-zinc.

A metal salt such as $PbSO_4$, $FeCl_2$ or $SnCl_2$, an alkali metal such as K or Na or an alkali metal salt, $BaSO_4$, or the like may be added to the Cu-containing hydrogenation catalyst. There are cases in which the addition improves the activity of the Cu-containing hydrogenation catalyst and the selection ratio for propylene. The amount of the metal salt, alkali metal or alkali metal salt to be added to the hydrogenation catalyst is not particularly restricted, and is preferably from 0.01% by mass to 10.00% by mass, mainly from the viewpoint of selectivity.

Examples of commercially available Cu-containing hydrogenation catalysts include $CuO$—$ZnO$—$Al_2O_3$, $CuO$—$Cr_2O_3$—$BaO$, etc.

The shape of the hydrogenation catalyst is not particularly restricted, and may be any of spherical, cylindrical, extruded and crushed shapes. The particle size thereof is not particularly restricted, either, and the hydrogenation catalyst may be chosen usually from those having sizes in a range of from 0.01 mm to 100 mm in accordance with the size of the reactor.

In the propylene production method according to the invention, the acetone and hydrogen may be supplied into a reactor filled with the hydrogenation catalyst and the solid acidic substance, and the acetone and hydrogen are allowed to react with each other. The total amount of the hydrogenation catalyst and the solid acidic substance filled into the reactor (hereinafter also referred to as "catalyst amount") is not particularly restricted. For example, in a case in which the reaction is carried out using a fixed bed flow device equipped with a fixed bed reactor, the value obtained by dividing the amount (mass) of acetone (starting material) supplied per unit of time by the catalyst amount (weight), which is WHSV, is preferably in a range of from 0.1 to 200/h, and further preferably in a range of from 0.2 to 100/h.

The quantitative ratio of the solid acidic substance to the hydrogenation catalyst is not particularly restricted, and, it is preferable that the ratio, solid acidic substance: hydrogenation catalyst (mass ratio), is usually from 1:0.01 to 1:100, and preferably from 1:0.05 to 1:50. There is a tendency that a quantitative ratio of solid acidic substance:hydrogenation catalyst of 1:(0.01 or more) provides a sufficient acetone conversion ratio. There is also a tendency that a quantitative ratio of solid acidic substance:hydrogenation catalyst of 1:(100 or less) allows the dehydration reaction to adequately proceed to afford a sufficient propylene yield.

In a case in which the activity of the catalysts decreases after the reaction is continued for a certain period of time, regeneration may be carried out using known methods, thereby recovering the activity of the hydrogenation catalyst and the solid acidic substance.

In the invention, the two components—the solid acidic substance and the hydrogenation catalyst—may be used as catalysts. Manners of usage of the catalysts are not particularly restricted. For example, the solid acidic substance, which is an acidic catalyst component, and the hydrogenation catalyst may be physically mixed on the level of centimeter-sized catalyst particles, or the solid acidic substance and the hydrogenation catalyst may be finely divided, mixed, and thereafter re-formed into centimeter-sized catalyst particles, or the hydrogenation catalyst may be retained on the solid acidic substance serving as a carrier, or the solid acidic substance may be retained on the hydrogenation catalyst serving as a carrier. Alternatively, the hydrogenation catalyst and the solid acidic substance may be individually used without being, for example, mixed with each other.

In particular, from the viewpoint of high activity, high selectivity and industrial availability, it is preferable to use the hydrogenation catalyst and to use β-zeolite as the zeolite for constituting the solid acidic substance. For example, the hydrogenation catalyst may be retained on zeolite. Examples of preparation methods therefor include: a method including impregnating zeolite with an aqueous solution of a nitrate salt of Cu and calcinating the resultant; a method including adding a complex in which organic molecules called ligand are attached to Cu for the purpose of providing the Cu with solubility in an organic solvent, to an organic solvent so as to prepare a solution, impregnating zeolite with the solution, and calcinating the resultant; a method including allowing the complex to be retained on zeolite by, for example, vapor deposition, in consideration of the fact that some complexes can be vaporized under vacuum; etc.

The hydrogenation catalyst may be retained on a carrier other than zeolite. Examples of carriers capable of retaining the hydrogenation catalyst include silica, alumina, silica-alumina, titania, magnesia, silica-magnesia, zirconia, zinc oxide, carbon (activated carbon), acid clay, diatomaceous earth, etc. Of these, it is preferable to select at least one selected from the group consisting of silica, alumina, silica-alumina, titania, magnesia, silica-magnesia, zirconia, zinc oxide and carbon (activated carbon), from the viewpoint of higher activity and higher selectivity, Examples of the reactor used in the invention include a fixed bed reactor, a fluidized bed reactor, etc. The fixed bed reactor is preferable from the viewpoint of preventing the wearing and disintegration of catalysts.

In the invention, methods for adding the hydrogenation catalyst and the solid acidic substance into the reactor is not particular restricted. When a fixed bed reactor is used as the reactor, the method for adding the hydrogenation catalyst and the solid acidic substance may significantly affect the reaction performance. As described above, it is surmised that hydrogenation and a dehydration reaction occur stepwise in the invention. Therefore, a method including sequentially adding catalyst species appropriate for the respective stages of the reaction into the reactor is a preferable filling method, in terms of efficient usage of the catalysts and suppression of undesired side reactions.

It is a behavior frequently observed in general chemical reactions that unexpected side reactions not observed at low hydrogen pressure or low reaction temperature occur particularly in the case of increasing the hydrogen pressure or the reaction temperature in order to increase the reaction rate. In such a case, the method for filling the catalysts, in particular, has a possibility of significantly affecting the reaction performance.

Accordingly, catalyst species appropriate for the respective stages of the reaction may be sequentially added into the reactor, or the hydrogenation catalyst and the solid acidic substance may be added into the reactor such that the mixing ratio of the hydrogenation catalyst and the solid acidic substance forms a gradient. Examples of methods for adding the hydrogenation catalyst and the solid acidic substance into the reactor include (1) a method in which the hydrogenation catalyst and the solid acidic substance are mixed and added into the reactor; (2) a method in which the addition into the reactor is carried out so as to form a layer formed by the hydrogenation catalyst (at the upstream side, i.e., the inlet side) and a layer formed by the solid acidic substance (at the downstream side, i.e., the outlet side); (3) a method in which a solid acidic substance on which the hydrogenation catalyst is retained is added into the reactor; (4) a method in which the addition into the reactor is carried out so as to form a layer formed by the hydrogenation catalyst (at the upstream side, i.e., the inlet side) and a layer formed by the solid acidic substance and the hydrogenation catalyst (at the downstream side, i.e., the outlet side); (5) a method in which the addition into the reactor is carried out so as to form a layer formed by the hydrogenation catalyst (at the upstream side, i.e., the inlet side) and a layer formed by a solid acidic substance on which the hydrogenation catalyst is retained (at the downstream side, i.e., the outlet side); (6) a method in which the addition into the reactor is carried out so as to form a layer formed by the hydrogenation catalyst and the solid acidic substance (at the upstream side, i.e., the inlet side) and a layer formed by the solid acidic substance (at the downstream side, i.e., the outlet side); and (7) a method in which the addition into the reactor is carried out so as to form a layer formed by a solid acidic substance on which the hydrogenation catalyst is retained (at the upstream side, i.e., the inlet side) and a layer formed by the solid acidic substance (at the downstream side, i.e., the outlet side). The upstream side refers to the inlet side of the reactor, i.e., a layer through which the starting materials pass in the former stage of the reaction, and the downstream side refers to the outlet side of the reactor, i.e., a layer through which the starting materials, intermediates, and reaction products pass in the latter stage of the reaction. The starting materials mean acetone and hydrogen. In a case in which acetone and hydrogen are supplied into the reactor by gas-liquid countercurrent flow, the upstream side (inlet side) means a layer through which acetone passes in the former stage of the reaction.

In order to maintain the propylene production amount, a merry-go-round method may be adopted in which two or three reactors are arranged in parallel, and, while the regeneration of catalysts is carried out in one of the reactors, reaction is carried out in the remaining one or two reactors. Further, in a case in which there are three reactors, a method may be used in which the remaining two reactors are connected in series, thereby reducing the variation in the production amount. In a case in which the invention is carried out using a fluidized bed flow reaction system or a moving bed reaction system, a constant activity can be maintained by continuously or intermittently removing a part or all of the catalysts from the reactor and replenishing an equivalent amount of the catalysts.

EXAMPLES

Examples of the invention are described below. However, the invention is by no means limited to these examples. As used herein, "%" is based on mass unless otherwise specified.

Preparation of Isopropyl Alcohol Producing Variant

Lists of the *Escherichia coli* variants and the plasmids used in the present examples are shown in Table 1 and Table 2.

TABLE 1

| Plasmid | Feature | Origin or Referenced Description |
|---------|---------|----------------------------------|
| pBRgapP | pBR322, containing GADPH promoter | Example 2 |
| pIa | pBRgapP-IPAdh-adc | Example 2 |
| pIaz | pBRgapP-IPAdh-adc-zwf | Example 2 |
| pIaaa | pBRgapP-IPAdh-adc-atoB-atoD-atoA | Example 4 |
| pTH18cs1 | Temperature-sensitive plasmid | GenBank AB019610 |

TABLE 2

| Escherichia coli | Feature | Origin or Referenced Description |
|---|---|---|
| B | wild type | ATCC11303 |
| MG1655 | wild type | ATCC |
| B::atoDAB | B strain, the promoter for atoDAB is replaced by GADPH promoter | Example 1 |
| BΔpgi | B strain, Δpgi | Example 3 |
| B::atoDABΔpgi | B strain, the promoter for atoDAB is replaced by GADPH promoter, Δpgi | Example 5 |
| B::atoDABΔgntR | B strain, the promoter for atoDAB is replaced by GADPH promoter, ΔgntR | Example 6 |
| B::atoDABΔpgiΔgntR | B strain, the promoter for atoDAB is replaced by GADPH promoter, Δpgi, ΔgntR | Example 9 |
| B::atoDABΔgnd | B strain, the promoter for atoDAB is replaced by GADPH promoter, Δgnd | Example 12 |
| B::atoDABΔpgiΔgnd | B strain, the promoter for atoDAB is replaced by GADPH promoter, Δpgi, Δgnd | Example 15 |
| B::atoDABΔgndΔgntR | B strain, the promoter for atoDAB is replaced by GADPH promoter, Δgnd, ΔgntR | Example 18 |
| B::atoDABΔpgiΔgndΔgntR | B strain, the promoter for atoDAB is replaced by GADPH promoter, Δpgi, Δgnd, ΔgntR | Example 21 |

Example 1

Preparation of B::atoDAB Variant

The entire base sequence of the genomic DNA of *Escherichia coli* MG1655 strain is known (GenBank accession number U00096), and the base sequence of a gene encoding CoA transferase α subunit (hereinafter sometimes abbreviated to "atoD") of *Escherichia coli* MG1655 strain has also been reported. That is, atoD is described in 2321469 to 2322131 of the *Escherichia coli* MG1655 strain genomic sequence, which is described in GenBank accession number U00096.

The promoter sequence of glyceraldehyde 3-phosphate dehydrogenase (hereinafter sometimes referred to as "GAPDH") from *Escherichia coli*, which is described in 397 to 440 in the base sequence information with a GenBank accession number X02662, can be used as the base sequence of a promoter necessary to express the above-mentioned gene. In order to obtain the GAPDH promoter, amplification by a PCR method was carried out using the genomic DNA of *Escherichia coli* MG1655 strain as a template and using cgctcaattgcaatgattgacacgattccg (SEQ ID NO: 1) and acagaat-tcgctatttgttagtgaataaaagg (SEQ ID NO: 2), and the DNA fragment obtained was digested with restriction enzymes MfeI and EcoRI, thereby obtaining a DNA fragment of about 100 bp encoding the GAPDH promoter. The obtained DNA fragment and a fragment obtained by digesting plasmid pUC19 (GenBank accession number X02514) with a restriction enzyme EcoRI followed by alkaline phosphatase treatment were mixed, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. Ten of the colonies obtained were individually cultured at 37° C. overnight in an LB liquid medium containing 50 μg/ml ampicillin, and plasmids were recovered, and plasmids from which the GAPDH promoter was not cut out when digested with restriction enzymes EcoRI and KpnI were selected. Further, the DNA sequence thereof was checked, and a plasmid in which the GAPDH promoter was properly inserted was named pUCgapP. The pUCgapP obtained was digested with restriction enzymes EcoRI and KpnI.

Furthermore, in order to obtain atoD, amplification by a PCR method was carried out using the genomic DNA of *Escherichia coli* MG1655 strain as a template and using cgaattcgctggtggaacatatgaaaacaaaattgatgacattacaagac (SEQ ID NO: 3) and gcggtaccttatttgctctcctgtgaaacg (SEQ ID NO: 4), and the DNA fragment obtained was digested with restriction enzymes EcoRI and KpnI, thereby obtaining an atoD fragment of about 690 bp. This DNA fragment was mixed with pUCgapP that had previously been digested with restriction enzymes EcoRI and KpnI. The mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. A plasmid was recovered from the bacterial cells obtained, and it was confirmed that atoD was properly inserted. The plasmid obtained was named pGAPatoD.

Here, *Escherichia coli* MG1655 strain is available from American Type Culture Collection.

As described above, the base sequence of atoD in the genomic DNA of *Escherichia coli* MG1655 strain has also been reported. PCR was carried out using the genomic DNA of *Escherichia coli* MG1655 strain as a template and using gactagatgctgaaatccactagtcttgtc (SEQ ID NO: 5) and tactg-cagcgttecagcaccttatcaacc (SEQ ID NO: 6), which were prepared based on the gene information of the 5' flanking region of atoD of *Escherichia coli* MG1655 strain, as a result of which a DNA fragment of about 1.1 kbp was amplified.

In addition, PCR was carried out using the expression vector pGAPatoD prepared above as a template and using ggtctagagcaatgattgacacgattccg (SEQ ID NO: 7) prepared based on the sequence information of the GAPDH promoter of *Escherichia coli* MG1655 strain and a primer of SEQ ID NO: 4 prepared based on the sequence information of atoD of *Escherichia coli* MG1655 strain, as a result of which a DNA fragment of about 790 bp having the GAPDH promoter and atoD was obtained.

The fragments obtained from the above were digested with restriction enzymes PstI and XbaI, and XbaI and KpnI, respectively, and the resultant fragments were mixed with a fragment obtained by digesting a temperature-sensitive plasmid pTH18cs1 (GenBank accession number AB019610) [Hashimoto-Gotoh, T., Gene, 241, 185-191 (2000)] with PstI and KpnI, and the mixed fragments were ligated using a ligase. Thereafter, DH5α strain was transformed with the ligation product, and transformants that grew on an LB agar plate containing 10 μg/ml chloramphenicol at 30° C. were obtained. The colonies obtained were cultured at 30° C. overnight in an LB liquid medium containing 10 μg/ml chloramphenicol, and a plasmid was recovered from the bacterial cells obtained. *Escherichia coli* B strain (ATCC11303) was transformed with the plasmid, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. The cultured bacterial cells obtained were applied to an LB agar plate containing 10 μg/ml chloramphenicol, and cultured at 42° C., as a result of which colonies were obtained. The colonies obtained were cultured at 30° C. for 2 hours in an antibiotic-free LB liquid medium, and applied to a antibiotic-free LB agar plate, as a result of which colonies that grew at 42° C. were obtained.

From the colonies that appeared, 100 colonies were randomly picked up, and each individually grown on an antibiotic-free LB agar plate and an LB agar plate containing 10 μg/mlchloramphenicol, and chloramphenicol-sensitive clones were selected. Furthermore, a fragment of about 790 bp that contained the GAPDH promoter and atoD was amplified, by PCR, from the chromosomal DNA of these clones, and a variant in which an atoD promoter region was replaced by the GAPDH promoter was selected. Then, a clone satisfying the above conditions was named *Escherichia coli* B::atoDAB.

Here, *Escherichia coli* B strain (ATCC11303) is available from the American Type Culture Collection, which is a bank of cells, microorganisms, and genes.

Example 2

Preparation of Plasmid pIaz

Acetoacetate decarboxylase of bacteria of the genus *Clostridium* is described in GenBank accession number M55392, and isopropyl alcohol dehydrogenase of the genus *Clostridium* is described in GenBank accession number AF157307.

The promoter sequence of glyceraldehyde 3-phosphate dehydrogenase (hereinafter sometimes referred to as "GAPDH") from *Escherichia coli*, which is described in 397 to 440 in the base sequence information with a GenBank accession number X02662, can be used as the base sequence of a promoter necessary to express the above-mentioned gene group.

In order to obtain the GAPDH promoter, amplification by a PCR method was carried out using the genomic DNA of *Escherichia coli* MG1655 strain as a template and using cgagctacatatgcaatgattgacacgattccg (SEQ ID NO: 18) and cgcgcgcatgctatttgttagtgaataaaagg (SEQ ID NO: 19), and the DNA fragment obtained was digested with restriction enzymes NdeI and SphI, as a result of which a DNA fragment of about 110 bp corresponding to the GAPDH promoter was obtained. The DNA fragment obtained was mixed with a fragment obtained by digesting plasmid pBR322 (GenBank accession number J01749) with restriction enzymes NdeI and SphI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmid pBRgapP was recovered from the bacterial cells obtained.

In order to obtain isopropyl alcohol dehydrogenase gene, amplification by a PCR method was carried out using the genomic DNA of *Clostridium beijerinckii* NRRL B-593 as a template and using aatatgcatgctggtggaacatat-gaaaggttttgcaatgctagg (SEQ ID NO: 8) and gcggatcct-tataatataactactgattaattaagtc (SEQ ID NO: 9), and the DNA fragment obtained was digested with restriction enzymes SphI and BamHI, as a result of which an isopropyl alcohol dehydrogenase fragment of about 1.1 kbp was obtained. The DNA fragment obtained was mixed with a fragment obtained by digesting plasmid pBRgapP with restriction enzymes SphI and BamHI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmids were recovered from the bacterial cells obtained, and it was confirmed that IPAdh was properly inserted. The plasmid obtained was named pGAP-IPAdh.

In order to obtain acetoacetate decarboxylase gene, amplification by a PCR method was carried out using the genomic DNA of *Clostridium acetobutylicum* ATCC824 as a template and using caggatccgctggtggaacatatgt-taaaggatgaagtaattaaacaaattagc (SEQ ID NO: 10) and ggaat-tcggtaccftacttaagataatcatatataacttcagc (SEQ ID NO: 11), and the DNA fragment obtained was digested with restriction enzymes BamHI and EcoRI, as a result of which an acetoacetate decarboxylase fragment of about 700 bp was obtained. The DNA fragment obtained was mixed with a fragment obtained by digesting the plasmid pGAP-IPAdh prepared above with restriction enzymes BamHI and EcoRI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmids were recovered from the bacterial cells obtained, and it was confirmed that adc was properly inserted. The plasmid obtained was named pIa.

In order to obtain glucose-6-phosphate 1-dehydrogenase gene (zwf), amplification by a PCR method was carried out using the genomic DNA of *Escherichia coli* B strain (GenBank accession No. CP000819) as a template, and the DNA fragment obtained was digested with restriction enzymes, as a result of which a glucose-6-phosphate 1-dehydrogenase fragment of about 1500 bp was obtained. The DNA fragment obtained was mixed with a fragment obtained by digesting the plasmid pIa prepared above with restriction enzymes, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and this plasmid was named pIaz.

Competent cells of *Escherichia coli* B::atoDAB prepared in Example 1 were transformed with the plasmid pIaz, and was cultured at 37° C. overnight on an LB Broth, Miller agar plate containing 50 μg/ml ampicillin, as a result of which *Escherichia coli* pIaz/B::atoDAB was obtained.

Example 3

Preparation of *Escherichia coli* B Strain Δpgi Variant

The entire base sequence of the genomic DNA of *Escherichia coli* MG1655 strain is known (GenBank accession number U00096), and the base sequence of a gene encoding phosphoglucose isomerase (hereinafter sometimes referred to as "pgi") of *Escherichia coli* has also been reported (Gen Bank accession number X15196). In order to clone a region flanking to the base sequence of the gene encoding pgi (1,650 bp), four types of oligonucleotide primers represented by caggaattcgctatatctggctctgcacg (SEQ ID NO: 14), cagtctagagcaatactcttctgattttgag (SEQ ID NO: 15), cagtctagatcatcgtcgatatgtaggcc (SEQ ID NO: 16) and gacctgcagatcatccgtcagctgtacgc (SEQ ID NO: 17) were synthesized. The primer of SEQ ID NO: 14 has an EcoRI recognition site in the 5'-terminal side thereof, each of the primers of SEQ ID NOs: 15 and 16 has an XbaI recognition site in the 5'-terminal side thereof, and the primer of SEQ ID NO: 17 has a PstI recognition site in the 5'-terminal side thereof.

The genomic DNA of *Escherichia coli* MG1655 strain (ATCC700926) was prepared, and PCR was carried out using the obtained genomic DNA as a template and using a primer pair of SEQ ID NO: 14 and SEQ ID NO: 15, as a result of which a DNA fragment of about 1.0 kb (hereinafter sometimes referred to as "pgi-L fragment") was amplified. In addition, PCR was also carried out using a primer pair of SEQ ID NO: 16 and SEQ ID NO: 17, as a result of which a DNA fragment of about 1.0 kb (hereinafter sometimes referred to as "pgi-R fragment") was amplified. These DNA fragments were separated by agarose electrophoresis, and collected. The pgi-L fragment was digested with EcoRI and XbaI, and the pgi-R fragment was digested with XbaI and PstI. The two types of digested fragments and a fragment obtained by digesting a temperature-sensitive plasmid pTH18cs1 (GenBank accession number AB019610) with EcoRI and PstI were mixed, and allowed to react using T4 DNA ligase. Thereafter, competent cells of *Escherichia coli* DH5α (manufactured by Toyobo Co., Ltd.) were transformed with the ligation product, and transformants that grew on an LB agar plate containing 10 μg/ml chloramphenicol at 30° C. were obtained. Plasmids were recovered from the transformants obtained, and it was confirmed that the two fragments—a 5'-upstream flanking region fragment and a 3'-downstream flanking region fragment of the gene encoding pgi—were properly inserted in pTH18cs1. The plasmid obtained was digested with XbaI, and then subjected to blunting treatment with T4 DNA polymerase. The resultant DNA fragment was mixed with a DNA fragment obtained by digesting pUC4K plasmid (GenBank accession number X06404) (Pharmacia) with EcoRI and further subjecting the obtained kanamycin-resistant gene to blunting treatment with a T4 DNA polymerase, and the mixed fragments were ligated using T4 DNA ligase. Subsequently, competent cells of *Escherichia coli* DH5α were transformed with the ligation product, and transformants that grew on an LB agar plate containing 10 μg/ml chloramphenicol and 50 μg/ml kanamycin at 30° C. were obtained. Plasmids were recovered from the transformants obtained, and it was confirmed that the kanamycin-resistant gene was properly inserted between the 5"-upstream flanking region fragment and the 3'-downstream flanking region fragment of the pgi-encoding gene. The plasmid obtained was named pTH18cs1-pgi.

*Escherichia coli* B strain (ATCC11303) was transformed with the thus-obtained plasmid pTH18cs1-pgi, and was cultured at 30° C. overnight on an LB agar plate containing 10 μg/ml chloramphenicol and 50 μg/ml kanamycin, as a result of which transformants were obtained. The transformants obtained were inoculated into an LB liquid medium containing 50 μg/ml kanamycin, and cultured at 30° C. overnight. Next, part of this culture liquid was applied to an LB agar plate containing 50 μg/ml kanamycin, as a result of which colonies that grew at 42° C. were obtained. The colonies obtained were cultured at 30° C. for 24 hours in an LB liquid medium containing 50 μg/ml kanamycin, and was applied to an LB agar plate containing 50 μg/ml kanamycin, as a result of which colonies that grew at 42° C. were obtained.

From the colonies that appeared, 100 colonies were randomly picked up, and each individually grown on an LB agar plate containing 50 μg/ml kanamycin and an LB agar plate containing 10 μg/ml chloramphenicol, and chloramphenicol-sensitive clones that grew only on the LB agar plate containing kanamycin were selected. Furthermore, the chromosomal DNAs of these target clones were amplified by PCR, and a variant from which a fragment of about 3.3 kbp indicating replacement of the pgi gene with the kanamycin-resistant gene could be amplified was selected. The variant obtained was named B strain pgi gene deletion variant (hereinafter sometimes abbreviated to "BΔpgi variant").

Here, *Escherichia coli* MG1655 strain and *Escherichia coli* B strain are available from American Type Culture Collection.

Examples 4

Preparation of pIaaa/BΔpgi Variant

The amino acid sequences and the base sequences of genes of thiolase and CoA transferase of *Escherichia coli* have already been reported. That is, the gene encoding thiolase is described in 2324131 to 2325315 of the *Escherichia coli* MG1655 strain genomic sequence described in GenBank accession number U00096. In addition, the gene encoding CoA transferase is described in 2321469 to 2322781 of the above-mentioned *Escherichia coli* MG1655 strain genomic sequence. Expression of these genes together with the later-described acetoacetate decarboxylase gene and isopropyl alcohol dehydrogenase gene from bacteria of the genus *Clostridium* enables production of isopropyl alcohol.

In order to obtain isopropyl alcohol dehydrogenase gene, amplification by a PCR method was carried out using the genomic DNA of *Clostridium beijerinckii* NRRL B-593 as a template and using aaatgcatgctggtggaacatatgaaaggattgcaatgctagg (SEQ ID NO: 20) and gcggatccggtaccttataatataactactgattaattaagtc (SEQ 11) NO: 21), and the DNA fragment obtained was digested with restriction enzymes SphI and BamHI, as a result of which an isopropyl alcohol dehydrogenase fragment of about 1.1 kbp was obtained. The DNA fragment obtained was mixed with a fragment obtained by digesting plasmid pBRgapP prepared in Example 2 with restriction enzymes SphI and BamHI, and the mixed fragments were ligated using a ligase. Thereafter, competent cells of *Escherichia coli* DH5α strain (Toyobo Co. Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmid pGAP-IPAdh was recovered from the bacterial cells obtained.

In order to obtain thiolase gene from *Escherichia coli*, amplification by a PCR method was carried out using the genomic DNA of *Escherichia coli* MG1655 strain as a template, and the DNA fragment obtained was digested with restriction enzymes, as a result of which a thiolase fragment of about 1.2 kbp was obtained. The DNA fragment obtained was mixed with a fragment obtained by digesting the plasmid pGAP-IPAdh prepared above with restriction enzymes, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 µg/ml ampicillin were obtained. The colonies obtained were cultured at 37° C. overnight in an LB liquid medium containing 50 µg/ml ampicillin, and plasmid pGAP-IPAdh-atoB was recovered from the bacterial cells obtained.

In order to obtain CoA transferase gene from *Escherichia coli*, amplification by a PCR method was carried out using the genomic DNA of *Escherichia coli* MG1655 strain as a template, and the DNA fragment obtained was digested with restriction enzymes, as a result of which a CoA transferase a subunit fragment of about 600 bp was obtained. The DNA fragment obtained was mixed with a fragment obtained by digesting the plasmid pGAP-IPAdh-atoB prepared above with restriction enzymes, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 µg/ml ampicillin were obtained. The colonies obtained were cultured at 37° C. overnight in an LB liquid medium containing 50 µg/ml ampicillin, and plasmid pGAP-IPAdh-atoB-atoD was recovered from the bacterial cells obtained.

Amplification by a PCR method was carried out using the genomic DNA of *Escherichia coli* MG1655 strain as a template, and the DNA fragment obtained was digested with restriction enzymes, as a result of which a CoA transferase β subunit fragment of about 600 bp was obtained. The DNA fragment obtained was mixed with a fragment obtained by digesting the plasmid pGAP-IPAdh-atoB-atoD prepared above with restriction enzymes, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 µg/ml ampicillin were obtained. The colonies obtained were cultured at 37° C. overnight in an LB liquid medium containing 50 µg/ml ampicillin, and plasmid pGAP-IPAdh-atoB-atoD-atoA was recovered from the bacterial cells obtained.

In order to obtain acetoacetate decarboxylase gene, amplification by a PCR method was carried out using the genomic DNA of *Clostridium acetobutylicum* ATCC824 as a template, and the DNA fragment obtained was digested with restriction enzymes, as a result of which an acetoacetate decarboxylase fragment of about 700 bp was obtained. The DNA fragment obtained was mixed with a fragment obtained by digesting the plasmid pGAP-IPAdh-atoB-atoD-atoA prepared above with restriction enzymes, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 µg/ml ampicillin were obtained. The colonies obtained were cultured at 37° C. overnight in an LB liquid medium containing 50 µg/ml ampicillin, and plasmid pGAP-IPAdh-Adc-atoB-atoD-atoA was recovered from the obtained bacterial cell, and was named pIaaa.

Competent cells of *Escherichia coli* BΔpgi prepared in Example 3 were transformed with the plasmid pIaaa, and was cultured at 37° C. overnight on an LB Broth, Miller agar plate containing 50 µg/ml ampicillin, as a result of which *Escherichia coli* pIaaa/BΔpgi variant was obtained.

Example 5

Preparation of B::atoDABΔpgi Variant

B::atoDAB prepared in Example 1 was transformed with pTH18s1-pgi prepared in Example 3, and cultured at 30° C. overnight on an LB agar plate containing 10 µg/ml chloramphenicol and 50 µg/ml kanamycin, as a result of which transformants were obtained. The transformants obtained were inoculated into an LB liquid medium containing 50 µg/ml kanamycin, and cultured at 30° C. overnight. Next, part of this culture liquid was applied to an LB agar plate containing 50 µg/ml kanamycin, as a result of which colonies that grew at 42° C. were obtained. The colonies obtained were cultured at 30° C. for 24 hours in an LB liquid medium containing 50 µg/ml kanamycin, and was applied to an LB agar plate containing 50 µg/ml kanamycin, as a result of which colonies that grew at 42° C. were obtained.

From the colonies that appeared, 100 colonies were randomly picked up, and each individually grown on an LB agar plate containing 50 µg/ml kanamycin and an LB agar plate containing 10 µg/ml chloramphenicol, and chloramphenicol-sensitive clones that grew only on the LB agar plate containing kanamycin were selected. Furthermore, the chromosomal DNAs of these target clones were amplified by PCR, and a variant from which a fragment of about 3.3 kbp indicating replacement of the pgi gene with the kanamycin-resistant gene could be amplified was selected. The variant obtained was named B strain atoD genome enhanced—pgi gene deletion variant (hereinafter sometimes abbreviated to "B::atoDABΔpgi variant").

Here, *Escherichia coli* MG1655 strain and *Escherichia coli* B strain are available from American Type Culture Collection.

Example 6

Preparation of B::atoDABΔgntR Variant

The entire base sequence of the genomic DNA of *Escherichia coli* B strain is known (GenBank accession No. CP000819), and the base sequence encoding GntR is described in 3509184 to 3510179 of the *Escherichia coli* B strain genomic sequence, which is described in GenBank accession No. CP000819. In order to clone a region flanking to a base sequence encoding GntR(gntR), four types of oligonucleotide primers represented by ggaattcgggtcaattttcaccctctatc (SEQ ID NO: 30), gtgggccgtcctgaaggtacaaaagagatagattctc (SEQ ID NO: 31), ctcttttgtaccttcaggacggcccacaaatttgaag (SEQ ID NO: 32) and ggaattcccagccccgcaaggccgatggc (SEQ ID NO: 33) were synthesized. Each of the primers of SEQ ID NOs: 30 and 33 has an EcoRI recognition site in the 5'-terminal side thereof.

The genomic DNA of *Escherichia coli* B strain (GenBank accession No. CP000819) was prepared, and PCR was carried out using the obtained genomic DNA as a template and using a primer pair of SEQ ID NO: 30 and SEQ ID NO: 31, as a result of which a DNA fragment of about 1.0 kb (hereinafter sometimes referred to as "gntR-L fragment") was amplified. In addition, PCR was carried out using a primer pair of SEQ ID NO: 32 and SEQ ID NO: 33, as a result of which a DNA fragment of about 1.0 kb (hereinafter sometimes referred to as "gntR-R fragment") was amplified. These DNA fragments were separated by agarose electrophoresis, and recovered. PCR was carried out using the gntR-L and gntR-R fragments as templates and using a primer pair of SEQ ID NO: 30 and SEQ ID NO: 33, as a result of which a DNA fragment of about 2.0 kb (hereinafter sometimes referred to as "gntR-LR fragment") was amplified. This gntR-LR fragment was separated by agarose electrophoresis, recovered, digested with EcoRI, and mixed with a fragment obtained by digesting a temperature-sensitive plasmid pTH18cs1 (GenBank accession number AB019610) with EcoRI. The mixed fragments were allowed to react using T4 DNA ligase. Thereafter, competent cells of Escherichia coli DH5α (manufactured by Toyobo Co., Ltd.) were transformed with the ligation product, and transformants that grew on an LB agar plate containing 10 μg/ml chloramphenicol at 30° C. were obtained. Plasmids were recovered from the transformants obtained, and it was confirmed that the gntLR fragment was properly inserted in pTH18cs1. The plasmid obtained was named pTH18cs1-gntR.

Escherichia coli B::atoDAB variant prepared in Example 1 was transformed with the thus-obtained plasmid pTH18cs1-gntR, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Next, part of this culture liquid was applied to an LB agar plate containing 10 μg/ml kanamycinan chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gntR gene could be amplified was selected. The variant obtained was named B strain atoD genome enhanced-gntR gene deletion variant (hereinafter sometimes abbreviated to "B::atoDABΔgntR variant").

Example 7

Preparation of pGAP-Ia/B::atoDABΔgntR Variant

Competent cells of Escherichia coli B::atoDABΔgntR variant prepared in Example 6 was transformed with the plasmid pIa prepared in Example 2, and cultured at 37° C. overnight on an LB Broth, Miller agar plate containing 50 μg/ml ampicillin, as a result of which Escherichia coli pIa/B::atoDABΔgntR variant was obtained.

Example 8

Preparation of pIaz/B::atoDABΔgntR Variant

Competent cells of Escherichia coli B::atoDABΔgntR variant prepared in Example 6 was transformed with the plasmid pIaz prepared in Example 2, and cultured at 37° C. overnight on an LB Broth, Miller agar plate containing 50 μg/ml ampicillin, as a result of which Escherichia coli pIaz/B::atoDABΔgntR variant was obtained.

Example 9

Preparation of B::atoDABΔpgiΔgntR Variant

Escherichia coli B::atoDABΔpgi variant prepared in Example 5 was transformed with the plasmid pTH18cs1-gntR prepared in Example 6, and cultured at 30° C. overnight on an LB Broth, Miller agar plate containing 10 μg/ml chloramphenicol, as a result of which transformants were obtained. The transformants obtained were inoculated into an LB liquid medium containing 10 μg/ml chloramphenicol, and cultured at 30° C. overnight. Next, part of this culture liquid was applied to an LB agar plate containing 10 μg/ml kanamycin chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gntR gene could be amplified was selected. The variant obtained was named B strain atoD genome enhanced-pgi gene deletion-gntR gene deletion variant (hereinafter sometimes abbreviated to "B::atoDABΔpgiΔgntR variant").

Here, Escherichia coli MG1655 strain and Escherichia coli B strain are available from American Type Culture Collection.

Example 10

Preparation of pIa/B::atoDABΔpgiΔgntR Variant

Competent cells of Escherichia coli B::atoDABΔpgiΔgntR variant prepared in Example 9 were transformed with the plasmid pIa prepared in Example 2, and cultured at 37° C. overnight on an LB Broth, Miller agar plate containing 50 μg/ml ampicillin, as a result of which Escherichia coli pIa/B::atoDABΔpgiΔgntR was obtained.

Example 11

Preparation of pIaz/B::atoDABΔpgiΔgntR Variant

Competent cells of Escherichia coli B::atoDABΔpgiΔgntR variant prepared in Example 9 were transformed with the plasmid pIaz prepared in Example 2, and cultured at 37° C. overnight on an LB Broth, Miller agar plate containing 50 μg/ml ampicillin, as a result of which Escherichia coli pIaz/B::atoDABΔpgiΔgntR variant was obtained.

Example 12

Preparation of B::atoDABΔgnd Variant

In order to clone a region flanking to the base sequence of a gene encoding phosphogluconate dehydrogenase (gnd), four types of oligonucleotide primers represented by cgc-catatgaatggcgcggcggggccggtgg (SEQ ID NO: 34), tggagctct-gtttactcctgtcaggggg (SEQ ID NO: 35), tggagctctctgatttaat-caacaataaaattg (SEQ ID NO: 36) and cgggatccaccaccataaccaaacgacgg (SEQ ID NO: 37) were synthesized. The primer of SEQ ID NO: 34 has an NdeI recognition site in the 5'-terminal side thereof, and each of the primers of SEQ ID NO: 35 and SEQ ID NO: 36 has a SacI recognition site in the 5'-terminal side thereof. Further, the primer of SEQ ID NO: 37 has a BamHI recognition site in the 5'-terminal side thereof.

The genomic DNA of *Escherichia coli* B strain (GenBank accession No. CP000819) was prepared, and PCR was carried out using a primer pair of SEQ ID NO: 34 and SEQ ID NO: 35, as a result of which a DNA fragment of about 1.0 kb (hereinafter sometimes referred to as "gnd-L fragment") was amplified. Also, PCR was carried out using a primer pair of SEQ ID NO: 36 and SEQ ID NO: 37, as a result of which a DNA fragment of about 1.0 kb (hereinafter sometimes referred to as "gnd-R fragment") was amplified. These DNA fragments were separated by agarose electrophoresis, and recovered. The gnd-L fragment was digested with NdeI and SacI, and the gnd-R fragment was digested with SacI and BamHI. These two types of digested fragments were mixed with a fragment obtained by digesting a temperature-sensitive plasmid pTH18cs1 (GenBank accession number AB019610) with NdeI and BamHI, and the mixed fragments were allowed to react using T4 DNA ligase. Thereafter, competent cells of *Escherichia coli* DH5α (manufactured by Toyobo Co., Ltd.) were transformed with the ligation product, and transformants that grew on an LB agar plate containing 10 μg/ml chloramphenicol at 30° C. were obtained. Plasmids were recovered from the transformants obtained, and it was confirmed that the two fragments of a 5'-upstream flanking region fragment and a 3'-downstream flanking region fragment of the gnd-encoding gene were properly inserted in pTH18cs1. The plasmid obtained was named pTH18cs1-gnd.

*Escherichia coli* B::atoDAB variant prepared in Example 1 was transformed with the thus-obtained plasmid pTH18cs1-gnd, and was cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Next, part of this culture liquid was applied to an LB agar plate containing 10 μg/ml kanamycinan chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gnd gene could be amplified was selected. The variant obtained was named B::atoDABΔgnd variant.

Here, *Escherichia coli* B strain are available from American Type Culture Collection.

Example 13

Preparation of pIa/B::atoDABΔgnd Variant

Competent cells of *Escherichia coli* B::atoDABΔgnd variant prepared in Example 12 were transformed with the plasmid pIa prepared in Example 2, and cultured at 37° C. overnight on an LB Broth, Miller agar plate containing 50 μg/ml ampicillin, as a result of which *Escherichia coli* pIa/B::atoDABΔgnd variant was obtained.

Example 14

Preparation of pIaz/B::atoDABΔgnd Variant

Competent cells of *Escherichia coli* B::atoDABΔgnd variant prepared in Example 12 were transformed with the plasmid pIaz prepared in Example 2, and cultured at 37° C. overnight on an LB Broth, Miller agar plate containing 50 μg/ml ampicillin, as a result of which *Escherichia coli* pIaz/B::atoDABΔgnd variant was obtained.

Example 15

Preparation of B::atoDABΔpgiΔgnd Variant

*Escherichia coli* B::atoDABΔpgi variant prepared in Example 5 was transformed with the plasmid pTH18cs1-gnd prepared in Example 12, and cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Next, part of this culture liquid was applied to an LB agar plate containing 10 μg/ml kanamycin chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gnd gene could be amplified was selected. The variant obtained was named B::atoDABΔpgiΔgnd variant.

Example 16

Preparation of pIa/B::atoDABΔpgiΔgnd Variant

Competent cells of *Escherichia coli* B::atoDABΔpgiΔgnd variant prepared in Example 15 were transformed with the plasmid pIa prepared in Example 2, and cultured at 37° C. overnight on an LB Broth, Miller agar plate containing 50 μg/ml ampicillin, as a result of which *Escherichia coli* pIa/B::atoDABΔpgiΔgnd was obtained.

Example 17

Preparation of pIaz/B::atoDABΔpgiΔgnd Variant

Competent cells of *Escherichia coli* B::atoDABΔpgiΔgnd variant prepared in Example 15 were transformed with the plasmid pIaz prepared in Example 2, and cultured at 37° C. overnight on an LB Broth, Miller agar plate containing 50 μg/ml ampicillin, as a result of which *Escherichia coli* pIaz/B::atoDABΔpgiΔgnd variant was obtained.

Example 18

Preparation of B::atoDABΔgndΔgntR Variant

Competent cells of *Escherichia coli* B::atoDABΔgnd variant prepared in Example 12 were transformed with the plasmid pTH18cs1-gntR prepared in Example 6, and cultured at 30° C. overnight on an LB agar plate containing 10 μg/ml chloramphenicol, as a result of which transformants were obtained. The transformants obtained were inoculated into an LB liquid medium containing 10 μg/ml chloramphenicol, and cultured at 30° C. overnight. Next, part of this culture liquid was applied to an LB agar plate containing 10 μg/ml kanamycin chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gntR gene could be amplified was selected. The variant obtained was named B::atoDABΔgndΔgntR variant.

Example 19

Preparation of pIa/B::atoDABΔgndΔgntR Variant

Competent cells of *Escherichia coli* B::atoDABΔgndΔgntR variant prepared in Example 18 were transformed with the plasmid pIa prepared in Example 2, and cultured at 37° C. overnight on an LB Broth, Miller agar plate containing 50 μg/ml ampicillin, as a result of which *Escherichia coli* pIa/B::atoDABΔgndΔgntR variant was obtained.

Example 20

Preparation of pIaz/B::atoDABΔgndΔgntR Variant

Competent cells of *Escherichia coli* B::atoDABΔgndΔgntR variant prepared in Example 18 were transformed with the plasmid pIaz prepared in Example 2, and cultured at 37° C. overnight on an LB Broth, Miller agar plate containing 50 μg/ml ampicillin, as a result of which *Escherichia coli* pIaz/B::atoDABΔgndΔgntR variant was obtained.

Example 21

Preparation of B::atoDABΔpgiΔgndΔgntR Variant

Competent cells of *Escherichia coli* B::atoDABΔpgiΔgnd variant prepared in Example 15 were transformed withe the plasmid pTH18cs1-gntR prepared in Example 6, and cultured at 30° C. overnight on an LB agar plate containing 10 μg/ml chloramphenicol, as a result of which transformants were obtained. The transformants obtained were inoculated into an LB liquid medium containing 10 μg/mlchloramphenicol, and cultured at 30° C. overnight. Next, part of this culture liquid was applied to an LB agar plate containing 10 μg/ml kanamycin chloramphenicol, as a result of which colonies that grew at 42° C. were obtained. The colonies obtained were cultured at 30° C. for 24 hours in an LB liquid medium, and was applied to an LB agar plate, as a result of which colonies that grew at 42° C. were obtained.

From the colonies that appeared, 100 colonies were randomly picked up, and each individually grown on an LB agar plate and an LB agar plate containing 10 μg/ml chloramphenicol, and chloramphenicol-sensitive clones were selected. Furthermore, the chromosomal DNAs of these target clones were amplified by PCR, and a variant from which a fragment of about 2.0 kbp indicating deletion of the gntR gene could be amplified was selected. The variant obtained was named B::atoDABΔpgiΔgndΔgntR variant.

Example 22

Preparation of pIa/B::atoDABΔpgiΔgndΔgntR Variant

Competent cells of *Escherichia coli* B::atoDABΔpgiΔgndΔgntR variant the prepared in Example 21 were transformed with the plasmid pIa prepared in Example 2, and cultured at 37° C. overnight on an LB Broth, Miller agar plate containing 50 μg/ml ampicillin, as a result of which *Escherichia coli* pIa/B::atoDABΔpgiΔgndΔgntR variant was obtained.

Example 23

Preparation of pIaz/B::atoDABΔpgiΔgndΔgntR Variant

Competent cells of *Escherichia coli* B::atoDABΔpgiΔgndΔgntR variant prepared in Example 21 were transformed with the plasmid pIaz prepared in Example 2, and cultured at 37° C. overnight on an LB Broth, Miller agar plate containing 50 μg/ml ampicillin, as a result of which *Escherichia coli* pIaz/B::atoDABΔpgiΔgndΔgntR variant was obtained.

Example 24

Preparation of pIa/B::atoDAB Variant

Competent cells of *Escherichia coli* B::atoDAB variant prepared in Example 1 were transformed with the plasmid pIa prepared in Example 2, and cultured at 37° C. overnight on an LB Broth, Miller agar plate containing 50 μg/ml ampicillin, as a result of which *Escherichia coli* pIa/B::atoDAB variant was obtained.

Example 25

Preparation of pIaz/B::atoDABΔpgi Variant

Competent cells of *Escherichia coli* B::atoDAB variantΔpgi prepared in Example 5 were transformed with the plasmid pIaz prepared in Example 2, and cultured at 37° C. overnight on an LB Broth, Miller agar plate containing 50 μg/ml ampicillin, as a result of which *Escherichia coli* pIaz/B::atoDAB-Δpgi variant was obtained.

Test Example 1

Production of Isopropyl Alcohol

In this example, isopropyl alcohol was produced using a production apparatus shown in FIG. 1 of the WO 2009/008377 pamphlet. The culture tank used was a tank having a capacity of 3 L and made of glass, and the trap tanks used were tanks having a capacity of 10 L and made of polypropylene. Into the trap tanks, water as a trap solution (trap water) in an amount of 9 L per tank was injected, and the two trap tanks were connected for use. The culture tank was equipped with a drain pipe, and the culture liquid increased by feeding of sugar and a neutralizer was discharged to outside the culture tank, as appropriate.

A list of variants used in the evaluation of isopropyl alcohol production is shown in Table 3.

TABLE 3

| Variant Name | Feature | Referenced Description |
|---|---|---|
| pIa/B::atoDAB | Containing IPA production system | Example 24 |
| pIaz/B::atoDAB | Containing IPA production system, high expression of zwf | Example 2 |
| pIaaa/BΔpgi | Containing IPA production system, Δpgi | Example 4 |
| pIaz/B::atoDABΔpgi | Containing IPA production system, high expression of zwf, Δpgi | Example 25 |
| pIa/B::atoDABΔgntR | Containing IPA production system, ΔgntR | Example 7 |
| pIaz/B::atoDABΔgntR | Containing IPA production system, high expression of zwf, ΔgntR | Example 8 |
| pIa/B::atoDABΔpgiΔgntR | Containing IPA production system, Δpgi, ΔgntR | Example 10 |
| pIaz/B::atoDABΔpgiΔgntR | Containing IPA production system, high expression of zwf, Δpgi, ΔgntR | Example 11 |
| pIa/B::atoDABΔpgiΔgnd | Containing IPA production system, Δpgi, Δgnd | Example 16 |
| pIa/B::atoDABΔgndΔgntR | Containing IPA production system, Δgnd, ΔgntR | Example 19 |
| pIaz/B::atoDABΔgndΔgntR | Containing IPA production system, high expression of zwf, Δgnd, ΔgntR | Example 20 |
| pIa/B::atoDABΔpgiΔgndΔgntR | Containing IPA production system, Δpgi, Δgnd, ΔgntR | Example 22 |
| pIaz/B::atoDABΔpgiΔgndΔgntR | Containing IPA production system, high expression of zwf, Δpgi, Δgnd, ΔgntR | Example 23 |

IPA refers to isopropyl alcohol

As preculture, each of the variants to be evaluated was individually inoculated into an Erlenmeyer flask having a capacity of 500 mL and containing 50 ml of an LB Broth, Miller culture liquid (Difco 244620) containing 50 μg/ml ampicillin, and cultured overnight at a culture temperature of 30° C. while stirring at 120 rpm. 45 ml of the preculture was transferred into a culture tank (culture device BMS-PI manufactured by ABLE corporation) having a capacity of 3 L and containing 855 g of a culture medium having the following composition, and was cultivated. The cultivation was carried out at an aeration volume of 0.9 L/min, a stirring rate of 550 rpm, a culture temperature of 30° C. and a pH of 7.0 (adjusted with $NH_3$ aqueous solution) under atmospheric pressure. A 50 wt/wt % glucose aqueous solution was added at a flow rate of 10 g/L/hour during the period from the initiation of the cultivation to 8 hours after the initiation of the cultivation, and, thereafter, the 50 wt/wt % glucose aqueous solution was added at a flow rate of 20 g/L/hour, as appropriate, such that the amount of glucose left in the culture tank was minimized. The bacterial culture liquid was sampled several times during the period from the initiation of the cultivation to 72 hours after the initiation of the cultivation, and, after the bacterial cells were removed by centrifugal operation, the amounts of isopropyl alcohol and acetone accumulated in the culture supernatants and trap waters obtained were measured by HPLC according to an ordinary method. Each of the measurement values is a sum of the amounts in the culture liquid and the two trap tanks after the cultivation. The results are shown in Table 4.

<Composition of Culture Medium>
Corn steep liquor (manufactured by Nihon Shokuhin Kako Co Ltd.): 20 g/L
$Fe_2SO_4 \cdot 7H_2O$: 0.1 g/L
$K_2HPO_4$: 2 g/L
$KH_2PO_4$: 2 g/L
$MgSO_4 \cdot 7H_2O$: 2 g/L
$(NH_4)_2SO_4$: 2 g/L
ADEKA NOL LG 126 (ADEKA Corporation) 0.1 g/L
(Balance: Water)

TABLE 4

| Variant Name | IPA Production Amount (g/L/72 h) | Acetone Production Amount (g/L/72 h) |
|---|---|---|
| pIa/B::atoDAB (negative control) | 48.7 | 27.6 |
| pIaz/B::atoDAB | 39.4 | 20.2 |
| pIaaa/BΔpgi | 0.0 | 0.0 |
| pIaz/B::atoDABΔpgi | 41.1 | 3.0 |
| pIa/B::atoDABΔgntR | 57.3 | 23.7 |
| pIaz/B::atoDABΔgntR | 33.3 | 25.0 |
| pIa/B::atoDABΔpgiΔgntR | 9.6 | 0.8 |
| pIaz/B::atoDABΔpgiΔgntR | 70.2 | 10.6 |
| pIa/B::atoDABΔpgiΔgnd | 2.6 | 0.2 |
| pIa/B::atoDABΔgndΔgntR | 28.6 | 28.4 |
| pIaz/B::atoDABΔgndΔgntR | 33.9 | 25.3 |
| pIa/B::atoDABΔpgiΔgndΔgntR | 0.8 | 0.0 |
| pIaz/B::atoDABΔpgiΔgndΔgntR | 75.6 | 14.1 |

As result of the evaluation, the amount of isopropyl alcohol produced by a negative control (pIa/B::atoDAB) was 48.7 g/L/72 h, and the amount produced by a gntR disruptant (pIa/B::atoDABΔgntR) was 57.3 g/L/72 h. From this result, it was found that the disruption of gntR provides an increased productivity that is about 1.2 times that of the negative control.

In addition, the production amount achieved by a variant in which gntR and pgi were disrupted and in which expression of zwf was enhanced (pIaz/B::atoDABΔpgiΔgntR) was 70.2 g/L/72 h, which indicates a productivity that is about 1.4 times that of the negative control. From this result, it was found that disruption of both gntR and pgi in combination with enhancement of the expression of zwf further improves the productivity as compared to the case of disruption of gntR alone.

In the case of disruption of pgi alone (pIaaa/BΔpgi), isopropyl alcohol was not produced at all. In the case of enhancement of zwf alone (pIaz/B::atoDAB), the production amount was 39.4 g/L/72 h, and the productivity was decreased rather than increased.

The production amounts in the case of disruption of gntR in combination with high expression of zwf (pIaz/B::atoD-ABΔgntR), in the case of disruption of pgi in combination with high expression of zwf (pIaz/B::atoDABΔpgi), and in the case of disruption of both pgi and gntR (pIa/B::atoDAB-ΔpgiΔgntR) were 33.3 g/L/72 h, 41.1 g/L/72 h, and 9.6 g/L/72 h, respectively, and the efficiency of isopropyl alcohol production was decreased rather than increased.

Therefore, in a case in which disruption or high expression of other factors is carried out in addition to the disruption of gntR, the effect in terms of improvement of productivity achieved by pIaz/B::atoDABΔpgiΔgntR variant is considered to be obtained when both of gntR and pgi are disrupted and zwf is highly expressed.

Further, in a case in which gnd is further disrupted in pIaz/B::atoDABΔpgiΔgntR variant exhibiting increased productivity, i.e., in a case in which pgi, gntR, and gnd are disrupted and zwf is highly expressed (pIaz/B::atoDABΔ-pgiΔgndΔgntR), the amount of isopropyl alcohol produced was 75.6 g/L/72 h, which indicates a high productivity that is higher than that achieved by pIaz/B::atoDABΔpgiΔgntR variant.

In the case of disruption of gnd alone, the amount of isopropyl alcohol produced was 45.5 g/L/72 h, which is lower than that achieved by the negative control. That is, the disruption of gnd alone did not exhibit an effect in terms of improvement of isopropyl alcohol production efficiency. The production amounts in the case of disruption of gntR and gnd (pIa/B::atoDABΔgndΔgntR), in the case of disruption of pgi and gnd (pIa/B::atoDABΔpgiΔgnd) and in the case of disruption of pgi, gntR and gnd (pIa/B::atoDABΔpgiΔgndΔgntR) were 28.6 g/L/72 h, 2.6 g/L/72 h, and 0.8 g/L/72 h, respectively, indicating that these variants exhibited decreased isopropyl alcohol production efficiency rather than increased isopropyl alcohol production efficiency. The efficiency of isopropyl alcohol production was decreased rather than increased also in a case in which gnd was disrupted and zwf was highly expressed (pIaz/B::atoDABΔgnd), in a case in which gntR and gnd were disrupted and zwf was highly expressed (pIaz/B::atoDABΔgndΔgntR), and in a case in which pgi and gnd were disrupted and zwf was highly expressed (pIaz/B::atoDABΔpgiΔgnd), and the productivities in such cases were 40.7 g/L/72 h, 33.9 g/L/72 h, and 34.9 g/L/72 h, respectively.

Therefore, the effect in terms of productivity improvement achieved by pIaz/B::atoDABΔpgiΔgndΔgntR variant is considered to be obtained only in a case in which gntR, pgi and gnd are simultaneously disrupted and in which zwf is strongly expressed.

In addition, the acetone obtained can be used as a raw material for isopropyl alcohol production, after purification thereof.

(Manufacture of Acetone)

Example 26

Recovery of Isopropyl Alcohol and Acetone

The trap water obtained when the culture evaluation of pIaz/B::atoDABΔpgiΔgndΔgntR variant (Example 23) was carried out was analyzed by gas chromatography (GC), and, as a result, it was found that 1.2 g/L of acetone and 4.3 g/L of isopropyl alcohol were contained. From the aqueous solution containing isopropyl alcohol and acetone (trap water sampled 72 hours after the initiation of the cultivation), isopropyl alcohol and acetone were recovered at higher concentrations by distillation.

Specifically, 2 L of the aqueous solution described above was first passed through a column filled with 250 ml of cation exchange resin (AMBERLYST 31 WET manufactured by Organo Corporation) at a flow rate of 500 ml/h, whereby residual ammonia etc. were removed. The resultant solution was distilled at normal pressure. A fraction obtained at boiling points of from 53 to 81.6° C. was sampled, and analyzed by GC, and found to contain 18.7% by mass of acetone, 62.6% by mass of isopropyl alcohol, 0.2% by mass of unidentified components and the balance water. The fraction was used as a raw material for the following dehydrogenation reaction.

Preparation of Dehydrogenation Catalyst $ZnO:ZrO_2$ (94:6)

15.94 g (0.15 mol) of sodium carbonate and 130 ml of water were added into a 500 ml round-bottom flask equipped with stirrer blades, to form a solution. To the resultant aqueous solution, an aqueous solution obtained by dissolving 34.36 g (0.11 mol) of zinc nitrate hexahydrate and 1.30 g (0.05 mol) of zirconium dinitrate oxide dihydrate in 150 ml of water was added dropwise over one and half hours. The resultant was left to stand for maturation for 5 days, and then filtered, and washed well with water. The resultant white matter was dried at 120° C. for 2 hours, and at 400° C. for 1 hour, and, lastly, calcinated at 600° C. for 2 hours. 9.50 g of a complex oxide catalyst, $ZnO:ZrO_2$ (94:6), was obtained as white powder.

Production of Acetone 1.0 g of the complex oxide catalyst $ZnO:ZrO_2$ (94:6) (compression-molded at 20 MPa and thereafter classified to be from 250 to 500 μm) was added into a reactor made of SUS having a diameter of 1 cm and a length of 40 cm, and the distillate obtained above (acetone: 18.7% by mass, isopropyl alcohol: 62.6% by mass, unidentified components: 0.2% by mass, the balance: water) was allowed to flow through the reactor at 350° C. at a rate of 1.50 g/hr under a nitrogen stream of 10 ml/min. An outlet port of the reactor was cooled, thereby trapping the reaction solution and the reaction gas. The product sampled at 5 hours after the initiation of the reaction was analyzed by gas chromatography, and, as a result, it was found that acetone was produced at high concentration as shown in Table 5. In Table 5, "IPA" represents isopropyl alcohol (the same shall apply hereinafter).

Example 27

The same procedures as in Example 26 were carried out, except that the reaction temperature was set to 400° C. The results are shown in Table 5. As shown in Table 5, acetone was produced at high concentration.

Example 28

Preparation of Dehydrogenation Catalyst $ZnO:ZrO_2$ (88:12)

15.94 g (0.15 mol) of sodium carbonate and 130 ml of water were added into a 500 ml round-bottom flask equipped with stirrer blades, to form a solution. To the resultant aqueous solution, an aqueous solution obtained by dissolving 32.86 g (0.11 mol) of zinc nitrate hexahydrate and 2.66 g (0.10 mol) of zirconium dinitrate oxide dihydrate in 150 ml of water was added dropwise over one and half hours. The resultant was left to stand for maturation for 5 days, and then filtered, and washed well with water. The resultant white matter was dried at 120° C. for 2 hours, and at 400° C. for 1 hour, and, lastly, calcinated at 600° C. for 2 hours. 9.94 g of a complex oxide catalyst, $ZnO:ZrO_2$ (88:12), was obtained as white powder.

Production of Acetone 1.0 g of the complex oxide catalyst $ZnO:ZrO_2$ (88:12) (compression-molded at 20 MPa and thereafter classified to be from 250 to 500 μm) was added into a reactor made of SUS having a diameter of 1 cm and a length of 40 cm, and the distillate obtained above (acetone: 18.7% by mass, isopropyl alcohol: 62.6% by mass, unidentified components: 0.2% by mass, the balance: water) was allowed to flow through the reactor at 350° C. at a rate of 1.50 g/hr under a stream of nitrogen of 10 ml/min. An outlet port of the reactor was cooled, thereby trapping the reaction solution and the reaction gas. The product sampled at 5 hours after the initiation of the reaction was analyzed by gas chromatography, and, as a result, it was found that acetone was produced at high concentration as shown in Table 5.

Example 29

The same procedures as in Example 28 were carried out, except that the reaction temperature was set to 400° C. The results are shown in Table 5. As shown in Table 5, acetone was produced at high concentration.

to 440 in the base sequence information with a GenBank accession number X02662, can be used as the base sequence of a promoter necessary to express the gene group mentioned above.

In order to obtain the GAPDH promoter, amplification by a PCR method was carried out using the genomic DNA of *Escherichia coli* MG1655 strain as a template and using cgagctacatatgcaatgattgacacgattccg (SEQ ID NO: 38) and cgcgcgcatgctatttgttagtgaataaaagg (SEQ ID NO: 39), and the DNA fragment obtained was digested with restriction enzymes NdeI and SphI, as a result of which a DNA fragment of about 110 bp corresponding to the GAPDH promoter was obtained. The DNA fragment obtained was mixed with a fragment obtained by digesting plasmid pBR322 (GenBank accession number J01749) with restriction enzymes NdeI and SphI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmid pBRgapP was recovered from the bacterial cells obtained.

In order to obtain a codon-modified isopropyl alcohol dehydrogenase gene (IPAdh*), a codon-modified isopropyl alcohol dehydrogenase gene was designed based on the amino acid sequence of the isopropyl alcohol dehydrogenase gene of *Clostridium beijerinckii* NRRL B-593, and the following DNA fragment (SEQ ID NO: 40) was prepared by DNA synthesis. The sequence thereof is shown below.

TABLE 5

| | | | IPA | Composition of products other than IPA (in terms of mol %/isopropyl alcohol) | | | | |
|---|---|---|---|---|---|---|---|---|
| | Catalyst | Reaction Temperature | Conversion Ratio (%) | Acetone | Propylene | Mesityl Oxide | Methyl Isobutyl Ketone | Others |
| Example 26 | $ZnO:ZrO_2$ (94:6) | 350° C. | 97.8 | 78.3 | 8.4 | 3.9 | 0.2 | 9.2 |
| Example 27 | $ZnO:ZrO_2$ (94:6) | 400° C. | 99.6 | 71.9 | 6.1 | 4.6 | 0.3 | 17.1 |
| Example 28 | $ZnO:ZrO_2$ (88:12) | 350° C. | 83.5 | 89.8 | 1.0 | 2.4 | 0.1 | 6.7 |
| Example 29 | $ZnO:ZrO_2$ (88:12) | 400° C. | 99.0 | 80.0 | 1.3 | 3.5 | 0.1 | 15.1 |

Codon Modification of Gene Contained in Isopropyl Alcohol-Producing *Escherichia coli*

The codon sequences of the isopropyl alcohol dehydrogenase gene and the acetoacetate dehydrogenase gene contained in isopropyl alcohol-producing *Escherichia coli* according to the invention were modified, and the efficiency in production of isopropyl alcohol and acetone was checked as described below.

Example 30

Preparation of Plasmid pI*a*z

An acetoacetate decarboxylase gene (adc) of *Clostridium* bacteria is described in GenBank accession number M55392, and an isopropyl alcohol dehydrogenase gene (IPAdh) is described in GenBank accession number AF157307.

The promoter sequence of glyceraldehyde 3-phosphate dehydrogenase (hereinafter sometimes referred to as "GAPDH") from *Escherichia coli*, which is described in 397

```
ATGAAAGGTTTTGCAATGCTGGGTATTAATAAGCTGGGCTGGATCGAAA

AAGAGCGCCCGGTTGCGGGTTCGTATGATGCGATTGTGCGCCCACTGGC

CGTATCTCCGTGTACCTCAGATATCCATACCGTTTTTGAGGGAGCTCTT

GGCGACCGCAAGAATATGATTTTAGGGCATGAAGCGGTGGGTGAAGTTG

TGGAGGTAGGCAGTGAAGTGAAGGATTTCAAACCTGGTGACCGTGTTAT

CGTCCCTTGCACAACCCCGGATTGGCGGTCTTTGGAAGTTCAGGCTGGT

TTTCAACAGCACTCAAACGGTATGCTCGCAGGATGGAAATTTTCCAACT

TCAAGGATGGCGTCTTTGGTGAGTATTTTCATGTGAATGATGCGGATAT

GAATCTTGCGATTCTGCCTAAAGACATGCCCCTGGAAAACGCTGTTATG

ATCACAGATATGATGACTACGGGCTTCCACGGAGCCGAACTTGCAGATA

TTCAGATGGGTTCAAGTGTAGTGGTCATTGGCATTGGCGCGGTTGGCCT

GATGGGGATAGCCGGTGCTAAATTACGTGGAGCAGGTCGGATCATTGGC
```

```
GTGGGGAGCCGCCCGATTTGTGTCGAGGCTGCCAAATTTTACGGGGCCA

CCGACATTTTGAATTATAAAAATGGTCATATCGTTGATCAAGTCATGAA

ACTGACGAACGGAAAAGGCGTTGACCGCGTGATTATGGCAGGCGGTGGT

AGCGAAACACTGTCCCAGGCCGTATCTATGGTCAAACCAGGCGGGATCA

TTTCGAATATAAATTATCATGGAAGTGGCGATGCGTTATTGATCCCGCG

TGTGGAATGGGGGTGCGGAATGGCTCACAAGACTATCAAAGGCGGTCTT

TGTCCCGGGGGACGTTTGAGAGCAGAGATGCTGCGAGATATGGTAGTGT

ACAACCGTGTTGATCTCAGCAAACTGGTCACGCATGTATATCATGGGTT

CGATCACATCGAAGAAGCCCTGTTACTGATGAAAGACAAGCCAAAAGAC

CTGATTAAAGCAGTAGTTATATTATAA
```

Amplification by a PCR method was carried out using the prepared DNA fragment as a template and using acatgcatgcatgaaaggttttgcaatgctg (SEQ ID NO: 41) and acgcgtcgact-tataatataactactgattaa (SEQ ID NO: 42), and the DNA fragment obtained was digested with restriction enzymes SphI and SalI, as a result of which a codon-modified isopropyl alcohol dehydrogenase fragment of about 1.1 kbp was obtained. The DNA fragment obtained was mixed with a fragment obtained by digesting plasmid pUC119 with restriction enzymes SphI and SalI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmids were recovered from the bacterial cells obtained, and it was confirmed that codon-modified IPAdh* was properly inserted. The plasmid obtained was named pUC-I*.

A IPAdh*-containing fragment obtained by digesting plasmid pUC-I* with restriction enzymes SphI and EcoRI was mixed with a fragment obtained by digesting plasmid pBRgapP with restriction enzymes SphI and EcoRI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmids were recovered from the bacterial cells obtained, and it was confirmed that codon-modified IPAdh* was properly inserted. The plasmid obtained was named pGAP-I*.

In order to obtain a codon-modified acetoacetate decarboxylase gene (adc*), a codon-modified acetoacetate decarboxylase gene was designed based on the amino acid sequence of the acetoacetate decarboxylase gene of *Clostridium acetobutylicum* ATCC824, and the following DNA fragment (SEQ ID NO: 43) was prepared by DNA synthesis. The sequence thereof is shown below.

```
ATGCTGAAAGATGAAGTGATTAAACAGATTAGCACGCCATTAACTTCGC

CTGCATTTCCGCGCGGTCCGTATAAATTTCATAATCGTGAATATTTTAA

CATTGTATACCGTACCGATATGGACGCCCTGCGTAAAGTTGTGCCAGAG

CCTCTGGAAATTGATGAGCCCTTAGTCCGGTTCGAAATCATGGCAATGC

ATGATACGAGTGGCCTGGGTTGCTATACAGAATCAGGTCAGGCTATTCC

CGTGAGCTTTAATGGTGTTAAGGGCGACTACCTTCACATGATGTATCTG

GATAACGAGCCGGCAATTGCCGTAGGTCGGGAATTAAGTGCATACCCTA

AAAAGCTCGGGTATCCAAAGCTGTTTGTGGATTCAGACACTCTGGTGGG

CACGTTAGACTATGGAAAACTGCGTGTTGCGACCGCGACAATGGGGTAC

AAACATAAAGCCCTGGATGCTAATGAAGCAAAGGATCAAATTTGTCGCC

CGAACTATATGTTGAAAATCATCCCCAATTATGACGGCTCCCCTCGCAT

ATGCGAGCTTATCAACGCGAAAATCACCGATGTTACCGTACATGAAGCT

TGGACAGGACCGACTCGACTGCAGTTATTCGATCACGCTATGGCGCCAC

TGAATGACTTGCCGGTCAAAGAGATTGTTTCTAGCTCTCACATTCTTGC

CGATATAATCTTGCCGCGCGCGGAAGTCATATACGATTATCTCAAGTAA
```

Amplification by a PCR method was carried out using the prepared DNA fragment as a template and using acgcgtcgacgctggttggtggaacatatgctgaaagatgaagtgatta (SEQ ID NO: 44) and gctctagattacttgagataatcgtatatga (SEQ ID NO: 45), and the DNA fragment obtained was digested with restriction enzymes SalI and XbaI, as a result of which a codon-modified acetoacetate decarboxylase fragment of about 700 bp was obtained. The DNA fragment obtained was mixed with a fragment obtained by digesting the plasmid pGAP-I* prepared above with restriction enzymes SalI and XbaI, and the mixed fragments were ligated using a ligase. Thereafter, competent cells of *Escherichia coli* DH5α strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmids were recovered from the bacterial cells obtained, and it was confirmed that adc* was properly inserted. The plasmid obtained was named pI*a*.

In order to obtain glucose-6-phosphate 1-dehydrogenase gene (zwl), amplification by a PCR method was carried out using the genomic DNA of *Escherichia coli* B strain (GenBank accession No. CP000819) as a template and using gctctagacggagaaagtcttatggcggtaacgcaaacagcccagg (SEQ ID NO: 46) and cgggatccttactcaaactcattccaggaacgac (SEQ ID NO: 47), and the DNA fragment obtained was digested with restriction enzymes BamHI and XbaI, as a result of which a fragment of the glucose-6-phosphate 1-dehydrogenase of about 1500 bp was obtained. The DNA fragment obtained was mixed with a fragment obtained by digesting the plasmid pI*a* prepared above with restriction enzymes XbaI and BamHI, and the mixed fragments were ligated using a ligase. Thereafter, competent cells of *Escherichia coli* DH5 strain (Toyobo Co., Ltd. DNA-903) were transformed with the ligation product, and transformants that grew on an LB agar plate containing 50 μg/ml ampicillin were obtained. The colonies obtained were cultured at 37° C. overnight in an LB liquid medium containing 50 μg/ml ampicillin, and plasmid pI*a*z was recovered from the bacterial cells obtained.

Example 31

Preparation of pI*a*/B::atoDABΔgntR Variant

Competent cells of *Escherichia coli* B::atoDABΔgntR variant prepared in Example 6 were transformed with the plasmid pI*a* prepared in Example 30, and cultured at 37° C. overnight on an LB Broth, Miller agar plate containing 50 µg/ml ampicillin, as a result of which *Escherichia coli* pI*a*/B::atoDABΔgntR variant was obtained.

Example 32

Preparation of pI*a*z/B::atoDABΔpgiΔgntR Variant

Competent cells of *Escherichia coli* B::atoDABΔpgiΔgntR variant prepared in Example 9 were transformed with the plasmid pIa* prepared in Example 30, and cultured at 37° C. overnight on an LB Broth, Miller agar plate containing 50 µg/ml ampicillin, as a result of which *Escherichia coli* pI*a*z/B::atoDABΔpgiΔgntR was obtained.

Example 33

Preparation of pI*a*z/B::atoDABΔpgiΔgndΔgntR Variant

Competent cells of *Escherichia coli* B::atoDABΔpgiΔgndΔgntR variant prepared in Example 21 were transformed with the plasmid pI*a*z prepared in Example 30, and cultured at 37° C. overnight on an LB Broth, Miller agar plate containing 50 µg/ml ampicillin, as a result of which *Escherichia coli* pI*a*z/B::atoDABΔpgiΔgndΔgntR variant was obtained.

Example 34

Preparation of pI*a*/B::atoDAB Variant

Competent cells of *Escherichia coli* B::atoDAB variant prepared in Example 1 were transformed with the plasmid pI*a* prepared in Example 30, and cultured at 37° C. overnight on an LB Broth. Miller agar plate containing 50 µg/ml ampicillin, as a result of which *Escherichia coli* pI*a*/B::atoDAB variant was obtained.

Test Example 2

Production of Isopropyl Alcohol

Evaluation of isopropyl alcohol production was carried out in the same manner as in the [Test Example 1] described above. A list of the variants used in the evaluation is shown in Table 6. In addition, the evaluation results are shown in Table 7.

TABLE 7

| Variant Name | IPA Production Amount (g/L/72 h) | Acetone Production Amount (g/L/72 h) |
|---|---|---|
| pI*a*/B::atoDAB | 64.1 | 36.3 |
| pI*a*/B::atoDABΔgntR | 75.5 | 31.2 |
| pI*a*z/B::atoDABΔpgiΔgntR | 92.5 | 14.0 |
| pI*a*z/B::atoDABΔpgiΔgndΔgntR | 99.7 | 18.6 |

Comparison of the results shown in Table 7 with the results shown in Table 4 demonstrates that modification to the codons of the isopropyl alcohol dehydrogenase gene and the acetoacetate dehydrogenase gene significantly improves the efficiency of isopropyl alcohol production.

Example 35

Production of Isopropyl Alcohol from Sucrose

A gene of invertase (cscA), which is an enzyme that degrades sucrose, was further introduced into pI*a*z/B::atoDABΔpgiΔgndΔgntR variant, and fermentative production of isopropyl alcohol from sucrose was carried out. Furthermore, acetone or propylene was produced from the resultant fermentation liquid.

Preparation of pI*a*z-cscA/B::atoDABΔpgiΔgndΔgntR Variant

The entire base sequence of the genomic DNA of *Escherichia coli* O157 strain is known (GenBank accession number AE005174), and the base sequence of a gene encoding invertase (hereinafter sometimes abbreviated to "cscA") of *Escherichia coli* O157 strain has also been reported. That is, cscA is described in 3274383 to 3275816 of the *Escherichia coli* O157 strain genomic sequence, which is described in GenBank accession number AE005174.

In order to obtain the cscA, amplification by a PCR method was carried out using the genomic DNA of *Escherichia coli* O157 strain as a template and using gctggtggaacatatgacgcaatctcgattgcatg (SEQ ID NO: 48) and ttaacccagttgccagagtgc (SEQ ID NO: 49), and the termini of the resultant DNA fragment were phosphorylated using T4 polynucleotide kinase, as a result of which a cscA fragment of about 1470 bp was obtained. This DNA fragment was mixed with a fragment obtained by digesting pI*a*z prepared in Example 30 with a restriction enzyme BamHI, blunting the termini thereof using T4 DNA polymerase and dephosphorylating the termini using alkaline phosphatase, and the mixed fragments were ligated using a ligase. Thereafter, competent cells of *Escherichia coli* DH5α strain (Toyobo Co., Ltd. DNA-903) were transformed with the ligation product, and transformants that

TABLE 6

| Variant Name | Feature | Referenced Description |
|---|---|---|
| pI*a*/B::atoDAB | Containing IPA production system (the codons of IPAdh and adc being modified) | Example 34 |
| pI*a*/B::atoDABΔgntR | Containing IPA production system (the codons of IPAdh and adc being modified), ΔgntR | Example 31 |
| pI*a*z/B::atoDABΔpgiΔgntR | Containing IPA production system (the codons of IPAdh and adc being modified), high expression of zwf, Δpgi, ΔgntR | Example 32 |
| pI*a*z/B::atoDABΔpgiΔgndΔgntR | Containing IPA production system (the codons of IPAdh and adc being modified), high expression of zwf, Δpgi, Δgnd, ΔgntR | Example 33 |

IPA refers to isopropyl alcohol grew on an LB agar plate containing 50 μg/ml ampicillin at 30° C. were obtained. Plasmids were recovered from the bacterial cells obtained, and a plasmid which was confirmed to have proper insertion of the cscA by binding between the 3'-terminal side of glucose-6-phosphate 1-dehydrogenase gene (zwf) and the 5'-terminal side of cscA was named pI*a*z-cscA.

Here, the genome of *Escherichia coli* O157 is available from the Institute for Reference Materials and Measurements.

Competent cells of *Escherichia coli* B::atoDABΔ-pgiΔgndΔgntR variant prepared in Example 21 were transformed with the plasmid pI*a*z-cscA prepared above, and cultured at 37° C. overnight on an LB Broth, Miller agar plate containing 50 μg/ml ampicillin, as a result of which *Escherichia coli* pI*a*z-cscA/B::atoDABΔpgiΔgndΔgntR variant was obtained.

Test Example 31

Production of Isopropyl Alcohol and Acetone

Production of isopropyl alcohol and acetone was carried out in the same manner as in [Test Example 1] described above, except that *Escherichia coli* prez-cscA/B::atoDABΔ-pgiΔgndΔgntR variant was used, and that 40 wt/wt % sucrose aqueous solution was used as a culture medium instead of the 50 wt/wt % glucose aqueous solution. As a result, production of 82.0 g/L of isopropyl alcohol and 23.7 g/L of acetone was observed 72 hours after the initiation of the cultivation. HPLC analysis of trap water from the first tank revealed that 0.14% by mass of acetone and 0.55% by mass of isopropyl alcohol were contained.

Recovery of Isopropyl Alcohol and Acetone

From the trap water containing isopropyl alcohol and acetone, isopropyl alcohol and acetone were recovered at high concentrations by distillation.

Specifically, 9 L of the aqueous solution described above was first passed through a column filled with 250 ml of cation exchange resin (AMBERLYST 31 WET manufactured by Organo Corporation) at a flow rate of 500 ml/h, whereby residual ammonia etc. were removed. The resultant solution was distilled at normal pressure. A fraction obtained at boiling points of from 53 to 81.6° C. was sampled, and analyzed by GC, and found to contain 19.1% by mass of acetone, 60.5% by mass of isopropyl alcohol, 0.5% by mass of unidentified components and the balance water. The fraction was used as a raw material for the dehydrogenation reactions in the following Examples 36 to 39, and for the propylene production in Example 40.

Example 36

Manufacture of Acetone

Preparation of Dehydrogenation Catalyst $ZnO:ZrO_2$ (94:6)

15.94 g (0.15 mol) of sodium carbonate and 130 ml of water were added into a 500 ml round-bottom flask equipped with stirrer blades, to form a solution. To the resultant aqueous solution, an aqueous solution obtained by dissolving 34.36 g (0.11 mol) of zinc nitrate hexahydrate and 1.30 g (0.05 mol) of zirconium dinitrate oxide dihydrate in 150 ml of water was added dropwise over one and half hours. The resultant was left to stand for maturation for 5 days, and then filtered, and washed well with water. The resultant white matter was dried at 120° C. for 2 hours, and at 400° C. for 1 hour, and, lastly, calcinated at 600° C. for 2 hours. 9.50 g of a complex oxide catalyst, $ZnO:ZrO_2$ (94:6), was obtained as white powder.

Production of Acetone 1.0 g of the complex oxide catalyst $ZnO:ZrO_2$ (94:6) (compression-molded at 20 MPa and thereafter classified to be from 250 to 500 μm) was added into a reactor made of SUS having a diameter of 1 cm and a length of 40 cm, and the distillate obtained above (acetone: 19.1% by mass, isopropyl alcohol: 60.5% by mass, unidentified components: 0.5% by mass, the balance: water) was allowed to flow through the reactor at 350° C. at a rate of 1.50 g/hr under a nitrogen stream of 10 ml/min. An outlet port of the reactor was cooled, thereby trapping the reaction solution and the reaction gas. The product sampled at 5 hours after the initiation of the reaction was analyzed by gas chromatography, and, as a result, it was found that acetone was produced at high concentration as shown in Table 8 even when a large amount of water, and acetone and isopropyl alcohol containing impurities from organisms were used. In Table 8, "IPA" represents isopropyl alcohol (the same shall apply hereinafter).

Example 37

The same procedures as in Example 36 were carried out, except that the reaction temperature was set to 400° C. The results are shown in Table 8. As shown in Table 8, acetone was produced at high concentration.

Example 38

Preparation of Dehydrogenation Catalyst $ZnO:ZrO_2$ (88:12)

15.94 g (0.15 mol) of sodium carbonate and 130 ml of water were added into a 500 ml round-bottom flask equipped with stirrer blades, to form a solution. To the resultant aqueous solution, an aqueous solution obtained by dissolving 32.86 g (0.11 mol) of zinc nitrate hexahydrate and 2.66 g (0.10 mol) of zirconium dinitrate oxide dihydrate in 150 ml of water was added dropwise over one and half hours. The resultant was left to stand for maturation for 5 days, and then filtered, and washed well with water. The resultant white matter was dried at 120° C. for 2 hours, and at 400° C. for 1 hour, and, lastly, calcinated at 600° C. for 2 hours. 9.94 g of a complex oxide catalyst, $ZnO:ZrO_2$ (88:12), was obtained as white powder.

Production of Acetone 1.0 g of the complex oxide catalyst $ZnO:ZrO_2$ (88:12) (compression-molded at 20 MPa and thereafter classified to be from 250 to 500 μm) was added into a reactor made of SUS having a diameter of 1 cm and a length of 40 cm, and the distillate obtained above (acetone: 19.1% by mass, isopropyl alcohol: 60.5% by mass, unidentified components: 0.5% by mass, the balance: water) was allowed to flow through the reactor at 350° C. at a rate of 1.50 g/hr under a stream of nitrogen of 10 ml/min. An outlet port of the reactor was cooled, thereby trapping the reaction solution and the reaction gas. The product sampled at 5 hours after the initiation of the reaction was analyzed by gas chromatography, and, as a result, it was found that acetone was produced at high concentration as shown in Table 8.

Example 39

The same procedures as in Example 38 were carried out, except that the reaction temperature was set to 400° C. The results are shown in Table 8. As shown in Table 8, acetone was produced at high concentration.

TABLE 8

| | Catalyst | Reaction Temperature | IPA Conversion Ratio (%) | Composition of products (in terms of mol %/IPA) | | | | |
|---|---|---|---|---|---|---|---|---|
| | | | | Acetone | Propylene | Mesityl Oxide | Methyl Isobutyl Ketone | Others |
| Example 36 | ZnO:ZrO$_2$ (94:6) | 350° C. | 95.9 | 79.2 | 7.5 | 3.2 | 0.1 | 10.0 |
| Example 37 | ZnO:ZrO$_2$ (94:6) | 400° C. | 99.9 | 72.0 | 5.2 | 4.4 | 0.1 | 18.3 |
| Example 38 | ZnO:ZrO$_2$ (88:12) | 350° C. | 81.1 | 90.0 | 0.8 | 2.0 | 0.1 | 7.1 |
| Example 39 | ZnO:ZrO$_2$ (88:12) | 400° C. | 98.5 | 81.2 | 1.7 | 4.0 | 0.1 | 13.0 |

Example 40

Production of Propylene

A pressurized liquid phase flow reaction by a down flow was carried out using the distillate obtained from the culture liquid described in Test Example 3 of Example 35 as a raw material and using a fixed bed reactor equipped with a high-pressure feed pump, a high-pressure hydrogen mass flow, a high-pressure nitrogen mass flow, an electric furnace, a reactor having a catalyst filling portion, and a back pressure valve.

First, 1.0 g of powder (classified into 250 to 500 µm) of a copper-zinc catalyst (manufactured by SudChemie, product name: SHIFTMAX 210, having the following element mass %: from 32% to 35% of Cu, from 35% to 40% of Zn, and from 6% to 7% of Al) as an upstream side catalyst layer was filled into a reactor made of SUS and having an inner diameter of 1 cm, from the outlet side of the reactor. After quartz wool for separating catalyst layers was further filled into the reactor, 1.0 g of β-zeolite (manufactured by Catalysts & Chemicals Industries Co., Ltd., prepared by compression molding at 20 MPa and subsequent classification into 250 to 500 µm) as a downstream side catalyst layer was filled into the reactor.

After the reactor was pressurized to 2.5 MPa with hydrogen, the distillate described above (acetone: 19.1% by mass, isopropyl alcohol: 60.5% by mass, unidentified components: 0.5% by mass, the balance: water) was allowed to flow from the reactor inlet side at 180° C. at a rate of 0.60 g/h under a hydrogen stream of 20 ml/min from the reactor inlet side. Nitrogen was introduced, at 200 ml/min, between the outlet of the reactor and the back pressure valve, using the high-pressure nitrogen mass flow. A gas-liquid separation tube was installed in a line just downstream the back pressure valve, and the collected gaseous component and liquid component were each individually analyzed by GC to quantify the products. The reaction results are shown in Table 9. As shown in Table 9, it was found that propylene was produced at high conversion ratio even in a case in which a large amount of water, and acetone and isopropyl alcohol containing impurities from organisms were used. In Table 9, "DIPE" represents diisopropyl ether.

TABLE 9

| Reaction Time | Residual Ratio/ (Acetone + IPA) | | Composition of products (in terms of mol %/IPA) | | | | |
|---|---|---|---|---|---|---|---|
| | Acetone | IPA | Propylene | Propane | Propylene Dimer | DIPE | Others |
| 10 | 1.0 | 1.2 | 98.1 | 0.3 | 0.1 | 1.0 | 0.5 |

The disclosure of Japanese Patent Application No. 2010-181150, filed Aug. 12, 2010, and the disclosure of Japanese Patent Application No. 2011-049531, filed Mar. 7, 2011, are incorporated herein by reference in their entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. An isopropyl alcohol-producing *Escherichia coli* comprising an isopropyl alcohol production system, wherein an activity of transcriptional repressor GntR is recombinantly inactivated, and the isopropyl alcohol-producing *Escherichia coli* comprises a group of auxiliary enzymes having an enzyme activity expression pattern with which isopropyl alcohol production capacity achieved by the inactivation of the GntR activity is maintained or enhanced.

2. The isopropyl alcohol-producing *Escherichia coli* according to claim 1, wherein the enzyme activity expression pattern of the group of auxiliary enzymes is selected from the group consisting of:

(1) maintenance of wild-type activities of glucose-6-phosphate isomerase (Pgi) activity, glucose-6-phosphate 1-dehydrogenase (Zwf) activity and phosphogluconate dehydrogenase (Gnd) activity;

(2) inactivation of glucose-6-phosphate isomerase (Pgi) activity and enhancement of glucose-6-phosphate 1-dehydrogenase (Zwf) activity; and (3) inactivation of glucose-6-phosphate isomerase (Pgi) activity, enhancement of glucose-6-phosphate 1-dehydrogenase (Zwf) activity and inactivation of phosphogluconate dehydrogenase (Gnd) activity.

3. The isopropyl alcohol-producing *Escherichia coli* according to claim 2, wherein the glucose-6-phosphate 1-dehydrogenase (Zwf) activity is derived from a gene encoding glucose-6-phosphate 1-dehydrogenase (Zwf) derived from a bacterium of the genus *Escherichia*.

4. The isopropyl alcohol-producing *Escherichia coli* according to claim 1, wherein the isopropyl alcohol production system is constituted by enzymes encoded from genes of acetoacetate decarboxylase, isopropyl alcohol dehydrogenase, CoA transferase and thiolase.

5. The isopropyl alcohol-producing *Escherichia coli* according to claim 4, wherein the acetoacetate decarboxylase is derived from *Clostridium acetobutylicum*, the isopropyl alcohol dehydrogenase is derived from *Clostridium beijerinckii*, and the CoA transferase and the thiolase are derived from *Escherichia coli*.

6. The isopropyl alcohol-producing *Escherichia coli* according to claim 4, wherein at least one selected from the group consisting of the isopropyl alcohol dehydrogenase and the acetoacetate decarboxylase is encoded from a gene or genes introduced as a modified gene or modified genes.

7. The isopropyl alcohol-producing *Escherichia coli* according to claim 6, wherein the modified gene of the isopropyl alcohol dehydrogenase has the nucleic acid sequence represented by SEQ ID NO: 40, and the modified gene of the acetoacetate decarboxylase has the nucleic acid sequence represented by SEQ ID NO: 43.

8. The isopropyl alcohol-producing *Escherichia coli* according to claim 4, further comprising at least a sucrose hydrolase gene from among sucrose non-phosphoenolpyruvate dependent phosphotransferase system (PTS) genes.

9. The isopropyl alcohol-producing *Escherichia coli* according to claim 1, wherein the isopropyl alcohol production system is constituted by enzymes encoded from genes of acetoacetate decarboxylase, isopropyl alcohol dehydrogenase, CoA transferase and thiolase, and each of the enzyme genes is independently derived from at least one prokaryote selected from the group consisting of a bacterium of the genus *Clostridium*, a bacterium of the genus *Bacillus* and a bacterium of the genus *Escherichia*.

10. A method of producing isopropyl alcohol, comprising culturing the isopropyl alcohol-producing *Escherichia coli* of claim 1 in a state in which the isopropyl alcohol-producing *Escherichia coli* of claim 1 contacts with a plant-derived raw material to produce isopropyl alcohol.

11. A method of producing acetone, comprising:
obtaining isopropyl alcohol by culturing the isopropyl alcohol-producing *Escherichia coli* of claim 1 in a state in which the isopropyl alcohol-producing *Escherichia coli* of claim 1 contacts with a plant-derived raw material; and
contacting the obtained isopropyl alcohol with a complex oxide as a catalyst that includes zinc oxide and at least one oxide containing a Group 4 element, and that is prepared by coprecipitation to produce acetone.

12. A method of producing propylene, comprising:
obtaining isopropyl alcohol mixed with acetone by culturing the isopropyl alcohol-producing *Escherichia coli* of claim 1 in a state in which the isopropyl alcohol-producing *Escherichia coli* of claim 1 contacts with a plant-derived raw material; and
contacting the isopropyl alcohol mixed with acetone, with a solid acidic substance and a Cu-containing hydrogenation catalyst as catalysts, at a reaction temperature within a range of from 50 to 300° C. to produce propylene.

13. The method of producing propylene according to claim 12, wherein the Cu-containing hydrogenation catalyst is a catalyst that further includes at least one element selected from the group consisting of Group 6, Group 12 and Group 13 elements.

14. The method of producing propylene according to claim 12, wherein the solid acidic substance is zeolite.

\* \* \* \* \*